US007994165B2

(12) United States Patent
McKinnell et al.

(10) Patent No.: US 7,994,165 B2
(45) Date of Patent: *Aug. 9, 2011

(54) ARYL ANILINE DERIVATIVES AS $\beta_2$ ADRENERGIC RECEPTOR AGONISTS

(75) Inventors: Robert Murray McKinnell, Millbrae, CA (US); John R. Jacobsen, San Mateo, CA (US); Sean G. Trapp, San Francisco, CA (US); Daisuke Roland Saito, Burlingame, CA (US)

(73) Assignee: Theravance, Inc., South San Francisco, CA (US)

( * ) Notice: Subject to any disclaimer, the term of this patent is extended or adjusted under 35 U.S.C. 154(b) by 164 days.

This patent is subject to a terminal disclaimer.

(21) Appl. No.: 12/574,066

(22) Filed: Oct. 6, 2009

(65) Prior Publication Data

US 2010/0087410 A1 Apr. 8, 2010

Related U.S. Application Data

(62) Division of application No. 11/033,198, filed on Jan. 11, 2005, now Pat. No. 7,622,467.

(60) Provisional application No. 60/535,784, filed on Jan. 12, 2004.

(51) Int. Cl.
*A61K 31/535* (2006.01)
*A61K 31/497* (2006.01)
*A61K 31/47* (2006.01)
*A61K 31/425* (2006.01)
*C07C 215/60* (2006.01)
*C07D 243/10* (2006.01)
*C07D 265/30* (2006.01)

(52) U.S. Cl. ............... 514/235.2; 514/253.07; 514/312; 514/367; 544/128; 544/363; 546/157; 548/179; 548/180

(58) Field of Classification Search ........................ None
See application file for complete search history.

(56) References Cited

U.S. PATENT DOCUMENTS

| 3,875,233 | A | 4/1975 | Bastian et al. |
|---|---|---|---|
| 4,021,485 | A | 5/1977 | Schromm et al. |
| 4,894,219 | A | 1/1990 | Baker et al. |
| 4,992,474 | A | 2/1991 | Skidmore et al. |
| 5,223,614 | A | 6/1993 | Schromm et al. |
| 5,434,304 | A | 7/1995 | Trofast et al. |
| 5,750,701 | A | 5/1998 | Beeley et al. |
| 6,265,581 | B1 | 7/2001 | Bell et al. |
| 6,268,533 | B1 | 7/2001 | Gao et al. |
| 6,541,669 | B1 | 4/2003 | Moran et al. |
| 6,576,793 | B1 | 6/2003 | Moran et al. |
| 6,653,323 | B2 | 11/2003 | Moran et al. |
| 6,670,376 | B1 | 12/2003 | Moran et al. |
| 6,747,043 | B2 | 6/2004 | Moran et al. |
| 6,759,398 | B2 | 7/2004 | Biggadike |
| 6,825,220 | B2 | 11/2004 | Jesudason et al. |
| 6,919,482 | B2 | 7/2005 | Moran et al. |
| 6,949,568 | B2 | 9/2005 | Moran et al. |
| 7,060,712 | B2 | 6/2006 | Axt et al. |
| 7,125,892 | B2 | 10/2006 | Moran et al. |
| 7,317,023 | B2 | 1/2008 | McKinnell et al. |
| 7,399,863 | B2 | 7/2008 | Linsell et al. |
| 7,402,673 | B2 | 7/2008 | Linsell et al. |
| 7,557,247 | B2 | 7/2009 | Stergiades et al. |
| 7,566,785 | B2 | 7/2009 | Linsell et al. |
| 7,582,765 | B2 | 9/2009 | Moran et al. |
| 7,662,815 | B2 * | 2/2010 | McKinnell et al. ........ 514/235.5 |
| 2002/0019378 | A1 | 2/2002 | Angell et al. |
| 2002/0022625 | A1 | 2/2002 | Walland et al. |
| 2002/0143034 | A1 | 10/2002 | Taniguchi et al. |
| 2004/0157830 | A1 | 8/2004 | Biggadike et al. |
| 2004/0167167 | A1 | 8/2004 | Mammen et al. |
| 2004/0180876 | A1 | 9/2004 | Biggadike et al. |
| 2004/0242890 | A1 | 12/2004 | Coe et al. |
| 2005/0075271 | A1 | 4/2005 | Linsell et al. |
| 2008/0113981 | A1 | 5/2008 | McKinnell et al. |

FOREIGN PATENT DOCUMENTS

| BE | 849 794 | 4/1977 |
|---|---|---|
| CH | 550 768 | 2/1972 |
| EP | 0 233 686 A2 | 8/1987 |
| EP | 0147 719 B1 | 7/1989 |
| EP | 0 196 849 A2 | 10/1996 |
| GB | 1040724 | 9/1966 |
| GB | 1 463 219 | 2/1977 |
| JP | 52-83379 | 7/1977 |
| JP | 52-83619 | 7/1977 |
| WO | WO 99/64035 A1 | 12/1999 |
| WO | WO 00/75114 A1 | 12/2000 |
| WO | WO 01/07026 A2 | 2/2001 |
| WO | WO 01/42193 A1 | 6/2001 |
| WO | WO 02/00622 A2 | 1/2002 |
| WO | WO 03/024439 A1 | 3/2003 |

(Continued)

OTHER PUBLICATIONS

Bompart et al., "Synthesis of new β-blocking analogs of bevantolol", Annales Pharmaceutiques Francaises, Volume Date 1984, 42(6), pp. 537-545 (1985) (in French with English abstract).
Bompart et al., "Synthesis of new β-blocker analogs of bevantolol or alprenolol", Annales Pharmaceutiques Francaises, vol. Date 1987, 45(5), pp. 379-387 (1988) (in French with English abstract).
Deyrup et al., "Structure-affinity profile of 8-hydroxycarbostyril-based agonists that dissociate slowly from the Beta2-adrenoceptor", Naunyn-Schmiedeberg's Arch Pharmacol (1999) 359:168-177.
Isogaya et al., "Binding Pockets of the $\beta_1$- and $\beta_2$-Adrenergic Receptors for Subtype-Selective Agonists"), Molecular Pharmacology, vol. 56, pp. 875-885 (1999).
Milecki et al., "Carbostyril Derivatives Having Potent β-Adrenergic Agonist Properties", J. Med. Chem, (1987), 30, 1563-1566.
Yokoi et al., "The Development of a Radioimmunoassay for Formoterol", Life Sciences, (1983) vol. 33, No. 17, pp. 1665-1672.
Yoshizaki et al., "Sympathomimetic Amines Having a Carbostyril Nucleus", J. Med. Chem., (1976), vol. 19, No. 9, pp. 1138-1142.

(Continued)

*Primary Examiner* — Peter O Sullivan
(74) *Attorney, Agent, or Firm* — Jeffrey A. Hagenah; Roberta P. Saxon

(57) ABSTRACT

The invention provides novel $\beta_2$ adrenergic receptor agonist compounds. The invention also provides pharmaceutical compositions comprising such compounds, methods of using such compounds to treat diseases associated with $\beta_2$ adrenergic receptor activity, and processes and intermediates useful for preparing such compounds.

20 Claims, 6 Drawing Sheets

FOREIGN PATENT DOCUMENTS

| | | |
|---|---|---|
| WO | WO 03/042164 A1 | 5/2003 |
| WO | WO 03/072539 A1 | 9/2003 |
| WO | WO 03/091204 A1 | 11/2003 |
| WO | WO 2004/002939 A2 | 1/2004 |
| WO | WO 2004/016578 A2 | 2/2004 |
| WO | WO 2004/089892 A2 | 10/2004 |

* cited by examiner

US 7,994,165 B2

ARYL ANILINE DERIVATIVES AS $\beta_2$ ADRENERGIC RECEPTOR AGONISTS

CROSS-REFERENCE TO RELATED APPLICATIONS

This application is a divisional application of U.S. Ser. No. 11/033,198 filed Jan. 11, 2005 now U.S. Pat. No. 7,622,467 which claims the benefit of U.S. Provisional Application No. 60/535,784, filed on Jan. 12, 2004, the disclosures of which are incorporated herein by reference in their entirety.

FIELD OF THE INVENTION

The invention is directed to novel $\beta_2$ adrenergic receptor agonists. The invention is also directed to pharmaceutical compositions comprising such compounds, methods of using such compounds to treat diseases associated with $\beta_2$ adrenergic receptor activity, and processes and intermediates useful for preparing such compounds.

BACKGROUND OF THE INVENTION $\beta_2$ adrenergic receptor agonists are recognized as effective drugs for the treatment of pulmonary diseases such as asthma and chronic obstructive pulmonary disease (including chronic bronchitis and emphysema). $\beta_2$ adrenergic receptor agonists are also useful for treating pre-term labor, and are potentially useful for treating neurological disorders and cardiac disorders. In spite of the success that has been achieved with certain $\beta_2$ adrenergic receptor agonists, current agents possess less than desirable duration of action, potency, selectivity, and/or onset. Thus, there is a need for additional $\beta_2$ adrenergic receptor agonists having improved properties, such as improved duration of action, potency, selectivity, and/or onset.

SUMMARY OF THE INVENTION

The invention provides novel compounds that possess $\beta_2$ adrenergic receptor agonist activity. Among other properties, compounds of the invention have been found to be potent and selective $\beta_2$ adrenergic receptor agonists. In addition, compounds of the invention have been found to possess a surprising and unexpectedly long duration of action, which is expected to allow for once-daily, or even less frequent, dosing.

Accordingly, this invention provides a compound of formula (I):

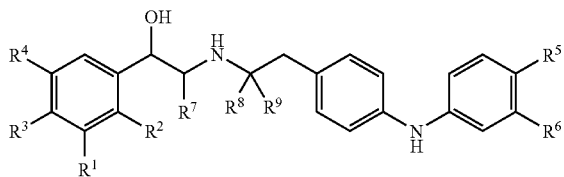

wherein:
each of $R^1$, $R^2$, $R^3$, and $R^4$ is independently selected from hydrogen, hydroxy, amino, halo, —$CH_2OH$ and —NHCHO, or $R^1$ and $R^2$ taken together are selected from —NHC(=O)CH=CH—, —CH=CHC(=O)NH—, —NHC(=O)S—; and —SC(=O)NH—;

one of $R^5$ and $R^6$ is —[X—$C_{1-6}$alkylenyl]$_n$-NR$^{10}$R$^{11}$ or $C_{1-6}$alkylenyl-NR$^{12}$R$^{13}$,
and the other of $R^5$ and $R^6$ is selected from hydrogen, hydroxy, $C_{1-4}$alkoxy, and $C_{1-4}$alkyl, wherein $C_{1-4}$alkyl is optionally substituted with halo,
wherein
each X is independently selected from —O—, —NH—, —S—, —NHSO$_2$—, —SO$_2$NH—, —NHC(=O)—, and —C(=O)NH—;
each of $R^{10}$, $R^{11}$, $R^{12}$, and $R^{13}$ is independently hydrogen or $C_{1-4}$alkyl; or
$R^{10}$ and $R^{11}$, together with the nitrogen atom to which they are attached, or $R^{10}$, together with the nitrogen atom to which it is attached and a carbon atom of the adjacent $C_{1-6}$alkylenyl, or $R^{12}$ and $R^{13}$, together with the nitrogen atom to which they are attached, or $R^{12}$, together with the nitrogen atom to which it is attached and a carbon atom of the adjacent $C_{1-6}$alkylenyl, form a heterocyclic or heteroaryl ring having from 5 to 7 ring atoms, and optionally containing an additional heteroatom selected from oxygen, nitrogen, and sulfur, wherein nitrogen is optionally substituted with —S(O)$_2$—$C_{1-4}$alkyl; and
n is 1, 2, or 3; and
each of $R^7$, $R^8$, and $R^9$ is independently hydrogen or $C_{1-6}$alkyl;
or a pharmaceutically-acceptable salt or solvate or stereoisomer thereof.

The invention also provides pharmaceutical compositions comprising a compound of the invention and a pharmaceutically-acceptable carrier. The invention further provides combinations comprising a compound of the invention and one or more other therapeutic agents and pharmaceutical compositions comprising such combinations.

The invention also provides a method of treating a mammal having a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation), the method comprising administering to the mammal, a therapeutically effective amount of a compound of the invention. The invention further provides a method of treatment comprising administering a therapeutically effective amount of a combination of a compound of the invention and one or more other therapeutic agents.

The invention also provides a method of treating a mammal having a disease or condition associated with $\beta_2$ adrenergic receptor activity, the method comprising administering to the mammal, a therapeutically effective amount of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate or stereoisomer thereof, as a research tool for studying a biological system or sample or for discovering new $\beta_2$ adrenergic receptor agonists.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a mammal having a disease or condition associated with $\beta_2$ adrenergic receptor activity (e.g. a pulmonary disease, such as asthma or chronic obstructive pulmonary disease, pre-term labor, a neurological disorder, a cardiac disorder, or inflammation).

DETAILED DESCRIPTION OF THE INVENTION

Figure 1:
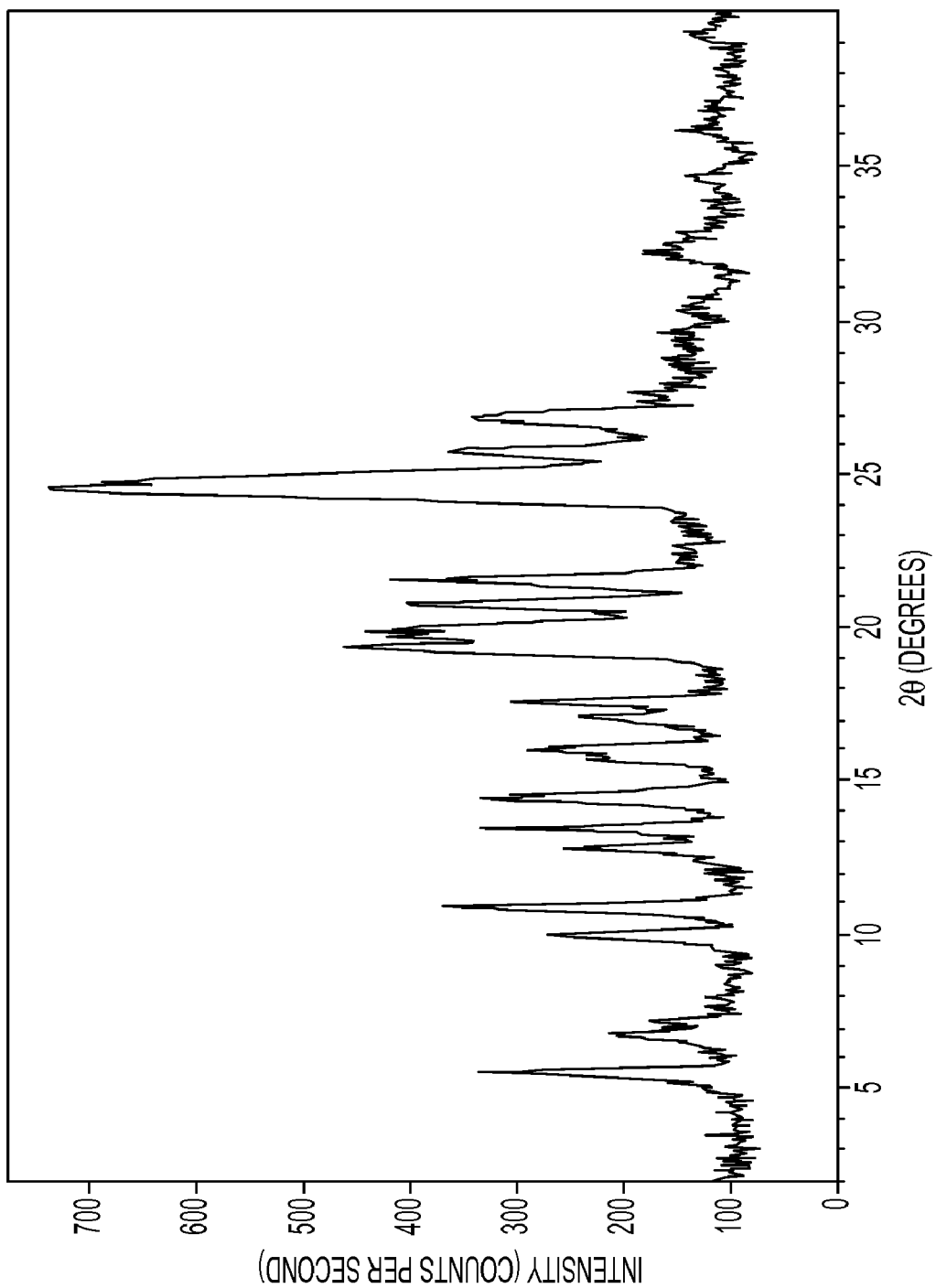
FIG. 1 is an x-ray powder diffraction pattern of the product of Example 17b.

The invention provides novel aryl aniline $\beta_2$ adrenergic receptor agonists of formula (I), or pharmaceutically-acceptable salts or solvates or stereoisomers thereof. The following substituents and values are intended to provide representative examples of various aspects of the invention. These representative values are intended to further define such aspects and are not intended to exclude other values or limit the scope of the invention.

In a specific aspect of the invention, $R^1$ is halo, —$CH_2OH$, or —NHCHO.

In other specific aspects, $R^1$ is chloro, —$CH_2OH$, or —NHCHO; or $R^1$ is —$CH_2OH$ or —NHCHO.

In a specific aspect, $R^2$ is hydrogen.

In a specific aspect, $R^3$ is hydroxy or amino.

In specific aspects, $R^4$ is hydrogen or halo; or $R^4$ is hydrogen or chloro.

In a specific aspect, $R^1$ is —NHCHO, $R^3$ is hydroxy, and $R^2$ and $R^4$ are each hydrogen.

In another specific aspect, $R^1$ and $R^2$ taken together are —NHC(=O)CH=CH— or —CH=CHC(=O)NH—, $R^3$ is hydroxy, and $R^4$ is hydrogen.

In another specific aspect, $R^1$ is —$CH_2OH$, $R^3$ is hydroxy, and $R^2$ and $R^4$ are each hydrogen.

In yet another specific aspect, $R^1$ and $R^4$ are chloro, $R^3$ is amino, and $R^2$ is hydrogen.

In still another specific aspect, $R^1$ and $R^2$ taken together are —NHC(=O)S— or —SC(=O)NH—, $R^3$ is hydroxy, and $R^4$ is hydrogen.

In a specific aspect, $R^5$ or $R^6$ is —[X—$C_{1-6}$alkylenyl]-$NR^{10}R^{11}$, where n, X, $R^{10}$ and $R^{11}$ are defined as in formula (I).

In another specific aspect, $R^5$ or $R^6$ is —[O—$C_{1-6}$allylenyl]$_n$-$NR^{10}R^{11}$ where $R^{10}$ and $R^{11}$ are defined as in formula (I) and n is 1 or 2.

In another specific aspect, $R^5$ or $R^6$ is —O—$C_{1-6}$alkylenyl-$NR^{10}R^{11}$ where each of $R^{10}$ and $R^{11}$ is independently hydrogen or $C_{1-4}$alkyl. Representative $R^5$ or $R^6$ values include, but are not limited to, —O($CH_2$)$_2NH_2$, —O($CH_2$)$_3N(CH_3$)$_2$, —O($CH_2$)$_4NH_2$, and —O$CH_2C(CH_3$)$_2NH_2$.

In another specific aspect, $R^5$ or $R^6$ is —O—$C_{1-6}$alkylenyl-$NR^{10}R^{11}$, where $R^{10}$ and $R^{11}$, together with the nitrogen atom to which they are attached, form a piperazinyl ring. For example, $R^5$ or $R^6$ is —O($CH_2$)$_2$-1-piperazinyl.

In yet another specific aspect, $R^5$ or $R^6$ is $C_{1-6}$alkylenyl-$NR^{12}R^{13}$ where $R^{12}$ and $R^{13}$ are defined as in formula (I).

In yet another specific aspect, $R^5$ or $R^6$ is $C_{1-6}$alkylenyl-$NR^{12}R^{13}$ where each of $R^{12}$ and $R^{13}$ is independently hydrogen or $C_{1-4}$alkyl. Representative $R^5$ or $R^6$ values within this aspect, include, but are not limited to, —($CH_2$)$_2NH_2$, —($CH_2$)$_2N(CH_3$)$_2$, and —$CH_2C(CH_3$)$_2NH_2$.

In still other specific aspects, $R^5$ or $R^6$ is $C_{1-4}$alkyl, optionally substituted with halo, for example, $CF_3$; or $R^5$ or $R^6$ is $C_{1-4}$alkoxy, for example, —$OCH_3$; or $R^5$ or $R^6$ is hydrogen; or $R^5$ or $R^6$ is hydroxy.

In a specific aspect, $R^7$ is hydrogen.

In a specific aspect, $R^8$ is hydrogen.

In a specific aspect, $R^9$ is hydrogen.

In one aspect, the invention provides a compound of formula (II):

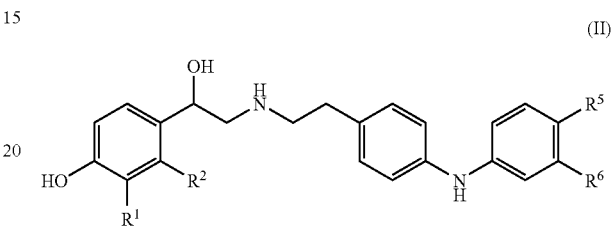

(II)

wherein:

$R^1$ is —$CH_2OH$ or —NHCHO, and $R^2$ is hydrogen; or $R^1$ and $R^2$ taken together are —NHC(=O)CH=CH— or —CH=CHC(=O)NH—;

one of $R^5$ and $R^6$ is —[O—$C_{1-6}$alkylenyl]$_n$-$NR^{10}R^{11}$ or $C_{1-6}$alkylenyl-$NR^{12}R^{13}$, and the other of $R^5$ and $R^6$ is selected from hydrogen, hydroxy, $C_{1-4}$alkoxy, and $C_{1-4}$alkyl, wherein $C_{1-4}$alkyl is optionally substituted with halo, wherein each of $R^{10}$, $R^{11}$, $R^{12}$, and $R^{13}$, is independently hydrogen or $C_{1-4}$alkyl; or $R^{10}$ and $R^{11}$, together with the nitrogen atom to which they are attached, or $R^{10}$, together with the nitrogen atom to which it is attached and a carbon atom of the adjacent $C_{1-6}$alkylenyl, or $R^{12}$ and $R^{13}$, together with the nitrogen atom to which they are attached, or $R^{12}$, together with the nitrogen atom to which it is attached and a carbon atom of the adjacent $C_{1-6}$alkylenyl, form a heterocyclic or heteroaryl ring having from 5 to 7 ring atoms and optionally containing an additional heteroatom selected from oxygen, nitrogen, and sulfur, wherein nitrogen is optionally substituted with —S(O)$_2$—$C_{1-4}$alkyl; and n is 1 or 2;

or a pharmaceutically-acceptable salt or solvate or stereoisomer thereof.

In another aspect, the invention provides compounds of formula (II) in which $R^5$ is —[O—$C_{1-6}$alkylenyl]$_n$-$NR^{10}R^{11}$ or $C_{1-6}$alkylenyl-$NR^{12}R^{13}$ and $R^6$ is hydrogen.

In another aspect, the invention provides compounds of formula (II) in which $R^5$ is $C_{1-4}$alkoxy and $R^6$ is —[O—$C_{1-6}$alkylenyl]$_n$-$NR^{10}R^{11}$ or $C_{1-6}$alkylenyl-$NR^{12}R^{13}$.

In another aspect, the invention provides compounds of formula (II) in which $R^5$ is selected from —O—$C_{1-6}$alkylenyl-$NR^{10}R^{11}$ and $C_{1-6}$alkylenyl-$NR^{12}R^{13}$ and $R^6$ is hydrogen; or $R^5$ is $C_{1-4}$alkoxy and $R^6$ is —$C_{1-6}$alkylenyl-$NR^{12}R^{13}$, wherein each of $R^{10}$, $R^{11}$, $R^{12}$ and $R^{13}$ is independently hydrogen or $C_{1-4}$, or $R^{10}$ and $R^{11}$, together with the nitrogen atom to which they are attached, form a piperazinyl ring.

A specific group of compounds within this aspect, is the group in which $R^1$ and $R^2$ taken together are —NHC(=O)CH=CH— or —CH=CHC(=O)NH—.

Another specific group of compounds within this aspect, is the group in which $R^5$ is —O—$C_{1-6}$alkylenyl-$NR^{10}R^{11}$ and $R^6$ is hydrogen.

In still other specific aspects, the invention provides compounds of formula (II) in which the variables $R^1$, $R^2$, $R^5$, and $R^6$ take the values listed in Table I below.

TABLE I

| Example No. | $R^1$ and $R^2$ | $R^5$ | $R^6$ |
|---|---|---|---|
| 1 | —NHC(=O)CH=CH— | —OCH$_2$C(CH$_3$)$_2$NH$_2$ | H |
| 2 | —NHC(=O)CH=CH— | —O(CH$_2$)$_2$NH$_2$ | H |
| 3 | —NHC(=O)CH=CH— | —O(CH$_2$)$_3$NH$_2$ | H |
| 4 | —NHC(=O)CH=CH— | —O(CH$_2$)$_4$NH$_2$ | H |
| 5 | —NHC(=O)CH=CH— | —O(CH$_2$)$_2$O(CH$_2$)$_2$NH$_2$ | H |
| 6 | —NHC(=O)CH=CH— | —O(CH$_2$)$_2$-4-morpholinyl | H |
| 7 | —NHC(=O)CH=CH— | —O(CH$_2$)$_2$-2-piperazinyl | H |
| 8 | —NHC(=O)CH=CH— | —OCH$_2$-1-pyridinyl | H |
| 9 | —NHC(=O)CH=CH— | —OCH$_2$C(CH$_3$)$_2$NH$_2$ | CF$_3$ |
| 10 | —NHC(=O)CH=CH— | —O(CH$_2$)$_2$-1,4-piperazinyl-SO$_2$CH$_3$ | H |
| 11 | —NHC(=O)CH=CH— | —(CH$_2$)$_2$NH$_2$ | H |
| 12 | —NHC(=O)CH=CH— | —(CH$_2$)N(CH$_3$)$_2$ | H |
| 13 | —NHC(=O)CH=CH— | —CH$_2$C(CH$_3$)$_2$NH$_2$ | H |
| 14 | $R^1$ = —NHCHO $R^2$ = H | —OCH$_2$C(CH$_3$)$_2$NH$_2$ | H |
| 15 | —NHC(=O)CH=CH— | —OCH$_3$ | —(CH$_2$)$_2$NH$_2$ |
| 16 | $R^1$ = —NHCHO $R^2$ = H | —OCH$_3$ | —(CH$_2$)$_2$NH$_2$ |

Particular mention may be made of the following compounds:

5-[(R)-2-(2-{4-[4-(2-amino-2-methyl -propoxy)-phenylamino]-phenyl}-ethylamino)-1-hydroxy-ethyl]-8-hydroxy-1H-quinolin-2-one;

8-hydroxy-5-[(R)-1-hydroxy-2-(2-{4-[4-(2-piperazin-1-yl-ethoxy)-phenylamino]-phenyl}-ethylamino)-ethyl]-1H-quinolin-2-one;

5-[(R)-2-(2-{4-[4-(2-amino-ethyl)-phenylamino]-phenyl}-ethylamino)-1-hydroxy-ethyl]-8-hydroxy-1H-quinolin-2-one;

5-[(R)-2-(2-{4-[4(2-dimethylamino-ethyl)-phenylamino]-phenyl}-ethylamino)-1-hydroxy-ethyl]-8-hydroxy-1H-quinolin -2-one;

5-[(R)-2-(2-{4-[3-(2-amino-ethyl)-4-methoxy -phenylamino]-phenyl}-ethylamino)-1-hydroxy-ethyl]-8-hydroxy-1H -quinolin-2-one; where the chemical nomenclature conforms to that of the automatic naming program AutoNom, as provided by MDL Information Systems, GmbH (Frankfurt, Germany).

As illustrated above, the compounds of the invention contain one or more chiral centers. Accordingly, the invention includes racemic mixtures, pure stereoisomers (i.e. individual enantiomers or diastereomers), and stereoisomer-enriched mixtures of such isomers, unless otherwise indicated. When a particular stereoisomer is shown, it will be understood by those skilled in the art, that minor amounts of other stereoisomers may be present in the compositions of this invention unless otherwise indicated, provided that the utility of the composition as a whole is not eliminated by the presence of such other isomers.

In particular, compounds of the invention contain a chiral center at the alkylene carbon in formulas (I) and (II) to which the hydroxy group is attached. When a mixture of stereoisomers is employed, it is advantageous for the amount of the stereoisomer with the (R) orientation at the chiral center bearing the hydroxy group to be greater than the amount of the corresponding (S) stereoisomer. When comparing stereoisomers of the same compound, the (R) stereoisomer is preferred over the (S) stereoisomer.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkoxy" means a monovalent group —O-alkyl, where alkyl is defined as above. Representative alkoxy groups include, by way of example, methoxy, ethoxy, propoxy, butoxy, and the like.

The term "alkenyl" means a monovalent unsaturated hydrocarbon group containing at least one carbon-carbon double bond, typically 1 or 2 carbon-carbon double bonds, and which may be linear or branched or combinations thereof. Unless otherwise defined, such alkenyl groups typically contain from 2 to 10 carbon atoms. Representative alkenyl groups include, by way of example, vinyl, allyl, isopropenyl, but-2-enyl, n-pent-2-enyl, n-hex-2-enyl, n-hept-2-enyl, n-oct-2-enyl, n-non-2-enyl, n-dec-4-enyl, n-dec-2,4-dienyl and the like.

The term "alkynyl" means a monovalent unsaturated hydrocarbon group containing at least one carbon-carbon triple bond, typically 1 carbon-carbon triple bond, and which may be linear or branched or combinations thereof. Unless otherwise defined, such alkynyl groups typically contain from 2 to 10 carbon atoms. Representative alkynyl groups include, by way of example, ethynyl, propargyl, but-2-ynyl and the like.

The term "alkylenyl" means a divalent saturated hydrocarbon group which may be linear or branched or combinations thereof. Unless otherwise defined, such alkylenyl groups typically contain from 1 to 10 carbon atoms. Representative alkylenyl groups include, by way of example, methylene, ethylene, n-propylene, n-butylene, propane-1,2-diyl (1-methylethylene), 2-methylpropane-1,2-diyl (1,1-dimethylethylene) and the like.

The term "heteroaryl" means a monovalent aromatic group having a single ring or two fused rings and containing in the ring at least one heteroatom (typically 1 to 3 heteroatoms) selected from nitrogen, oxygen, and sulfur. Unless otherwise defined, such heteroaryl groups typically contain from 5 to 10 total ring atoms. Representative heteroaryl groups include, by way of example, pyrroyl, isoxazolyl, isothiazolyl, pyrazolyl, pyridyl (or, equivalently, pyridinyl), oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, quinolyl, indolyl, isoquinolyl and the like, where the point of attachment is at any available carbon or nitrogen ring atom.

The term "heterocyclyl" or "heterocyclic ring" means a monovalent saturated or partially unsaturated cyclic non-aromatic group, which may be monocyclic or multicyclic (i.e., fused or bridged), and which contains at least one heteroatom (typically 1 to 3 heteroatoms) selected from nitrogen, oxygen, and sulfur. Unless otherwise defined, such heterocyclyl groups typically contain from 5 to 10 total ring atoms. Representative heterocyclyl groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl, and the like.

The term "halo" means fluoro, chloro, bromo or iodo.

The term "treatment" as used herein means the treatment of a disease or medical condition in a patient, such as a mammal (particularly a human) which includes:
 (a) preventing the disease or medical condition from occurring, i.e., prophylactic treatment of a patient;
 (b) ameliorating the disease or medical condition, i.e., eliminating or causing regression of the disease or medical condition in a patient;
 (c) suppressing the disease or medical condition, i.e., slowing or arresting the development of the disease or medical condition in a patient; or
 (d) alleviating the symptoms of the disease or medical condition in a patient.

The term "therapeutically effective amount" means an amount sufficient to effect treatment when administered to a patient in need of treatment.

The phrase "disease or condition associated with $\beta_2$ adrenergic receptor activity" includes all medical conditions alleviated by treatment with $\beta_2$ adrenergic receptor agonist and includes all disease states and/or conditions that are acknowledged now, or that are found in the future, to be associated with $\beta_2$ adrenergic receptor activity. Such disease states include, but are not limited to, pulmonary diseases, such as asthma and chronic obstructive pulmonary disease (including chronic bronchitis and emphysema), as well as neurological disorders and cardiac disorders. $\beta_2$ adrenergic receptor activity is also known to be associated with pre-term labor (see U.S. Pat. No. 5,872,126) and some types of inflammation (see International Patent Application Publication Number WO 99/30703 and U.S. Pat. No. 5,290,815).

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include, but are not limited to, acetic, benzenesulfonic, benzoic, camphosulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), 1,5-naphthalene disulfonic, cinnamic, and the like. Salts derived from fumaric, hydrobromic, hydrochloric, acetic, sulfuric, methanesulfonic, 1,5-naphthalene disulfonic, xinafoic, oxalic, tartaric, and 4-methyl-cinnamic acids are of particular interest.

Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate of stereoisomer thereof" is intended to include all permutations of salts, solvates and stereoisomers, such as a solvate of a pharmaceutically-acceptable salt of a stereoisomer of a compound of formula (I).

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of formulas (I) and (II) are prepared as illustrated in Scheme A. (The substituents and variables shown in the following schemes have the definitions provided above unless otherwise indicated.)

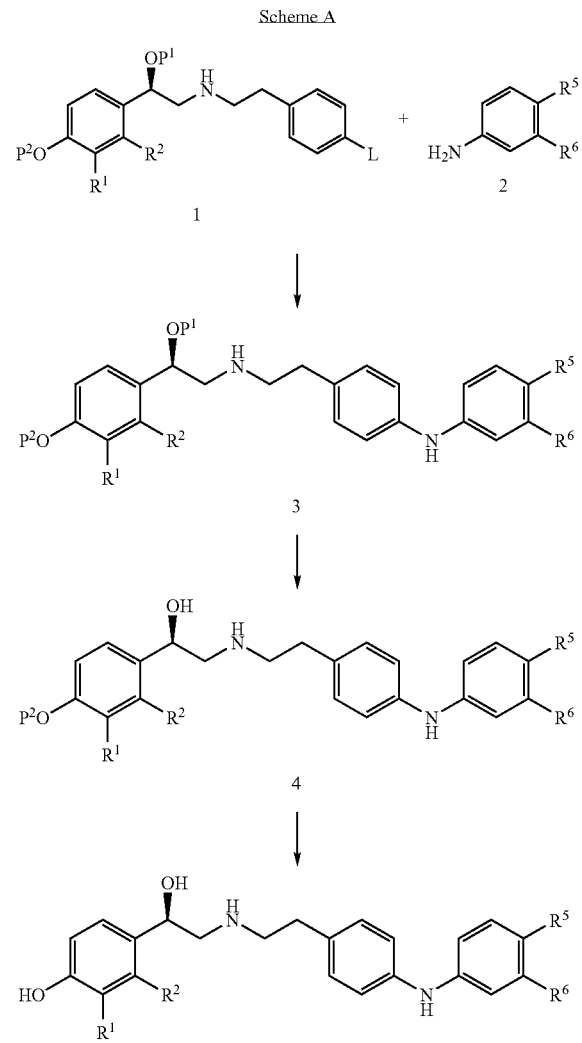

where $P^1$ represents a hydroxy-protecting group, $P^2$ represents a hydroxy-protecting group, and L represents a leaving group, such as bromo.

As shown in Scheme A, a compound of formula 1 is first reacted with an aryl amine (2) to provide an intermediate of formula 3. Typically, this reaction is conducted in an organic solvent in the presence of base and a transition metal catalyst and arylphosphine ligand with heating. A useful catalyst for coupling of an aryl group to an aryl amine is tris(dibenzylidenacetone)dipalladium(0) together with rac-2,2'-bis(diphenylphosphino)-1,1'-binapthyl. The reaction is typically heated at a temperature of between about 50° C. and about 120° C. for between about 0.25 and about 12 hours. The protecting group $P^1$ is typically a silyl protecting group, which is typically removed from the intermediate of formula 3 using a fluoride or acid reagent, to provide an intermediate of formula 4. The protecting group $P^2$ is typically a benzyl protecting group, which is typically removed from the intermediate of formula 4 by hydrogenation using a palladium on carbon catalyst, to provide the product.

An alternative method of preparing intermediate 3 is illustrated in Scheme B.

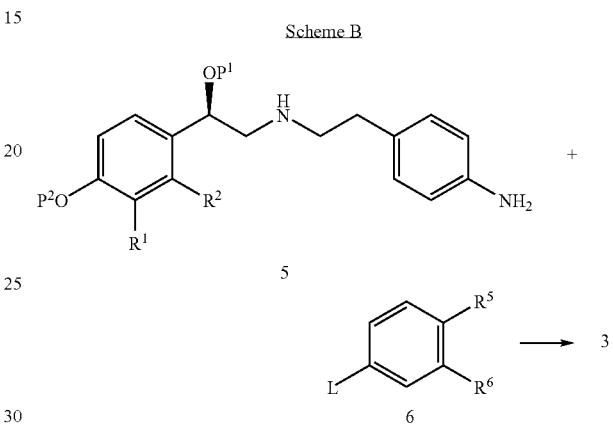

The conditions for the coupling of intermediates 5 and 6 in Scheme B to produce intermediate 3 are typically the same as those used to couple intermediates 1 and 2 in Scheme A.

Yet another alternative method of preparing intermediate 3 is illustrated in Scheme C.

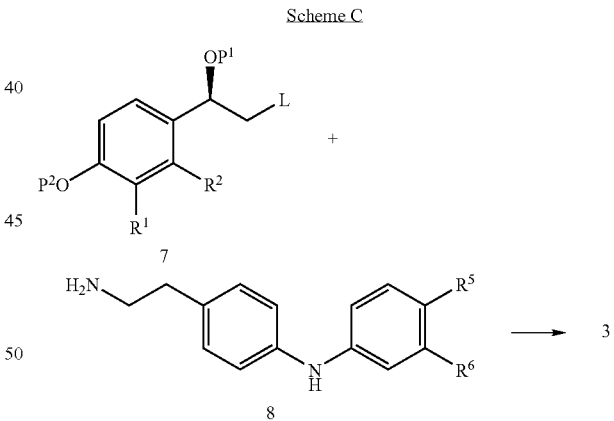

The reaction of Scheme C is typically conducted in a polar aprotic solvent in the presence of base. Typical suitable solvents include dimethylsulfoxide, dimethyl formamide, dimethylacetamide and the like. The reaction is typically heated at a temperature of between about 60° C. and about 140° C. for between about 0.25 and about 4 hours.

The compounds of formula 1 and 7 employed in the reactions described in this application are readily prepared by procedures known in the art, and described, for example, in U.S. Pat. Nos. 6,653,323 B2 and 6,670,376 B1, which are incorporated herein by reference, and references therein. Intermediate 5 can be prepared by reaction of intermediate 7 with 2-(4-aminophenyl)ethylamine in an aprotic solvent with heating.

Intermediates 2 and 6 are available commercially or are prepared from readily available starting materials. For example, when $R^5$ is —[O—$C_{1-6}$alkylenyl]$_n$-$NR^{10}R^{11}$ and $R^6$ is hydrogen, intermediate 2', of general formula 2, can be prepared by the process of Scheme D

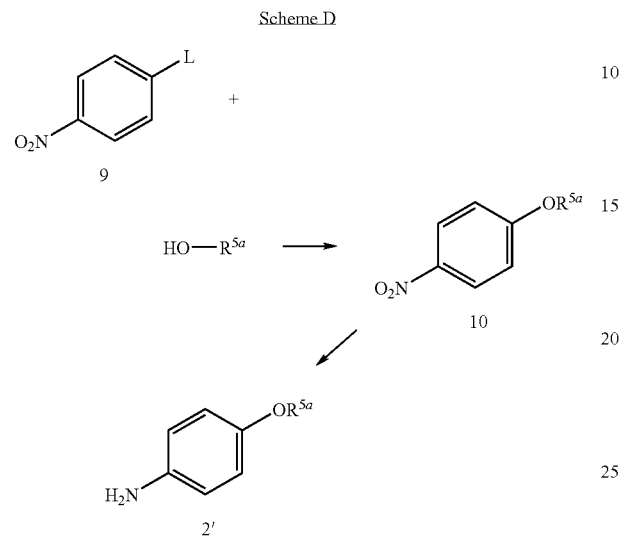

where $R^{5a}$ is defined such that —$OR^{5a}$ is —[O—$C_{1-6}$alkylenyl]$_n$-$NR^{10}R^{11}$. As one example of suitable reaction conditions for Scheme D, the reaction is conducted in dimethylsulfoxide in the presence of sodium hydride.

When, for example, $R^5$ is $C_{1-6}$alkylenyl-$NR^{12}R^{13}$ and $R^6$ is hydrogen, intermediate 2", of general formula 2, can be prepared by the process of Scheme E

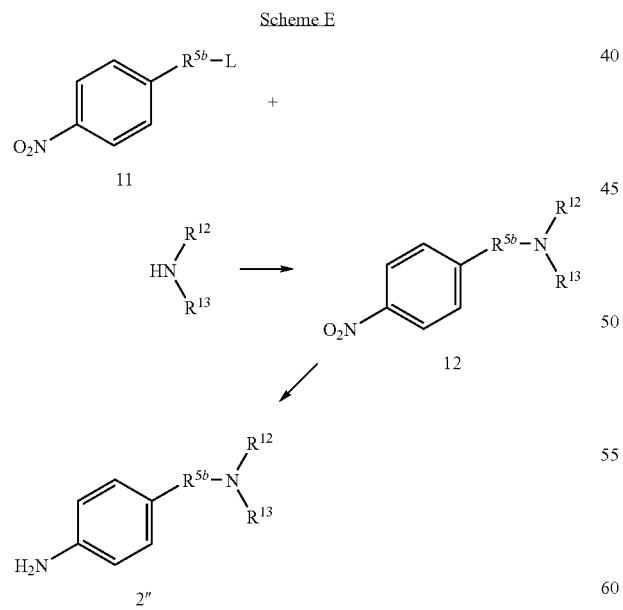

where $R^{5b}$ is $C_{1-6}$alkylenyl.

An intermediate of formula 8 can be prepared by reacting an intermediate of formula 2 with a phenethylamine substituted with a leaving group at the 4-position of the phenyl ring, for example, 4-bromophenethylamine.

Further details regarding specific reaction conditions and other procedures for preparing representative compounds of the invention or intermediate thereto are described in the Examples below.

Accordingly, in a method aspect, the invention provides a process for preparing a compound of formula (I), or a salt or stereoisomer or protected derivative thereof, the process comprising:

(a) reacting
(i) a compound of formula (III):

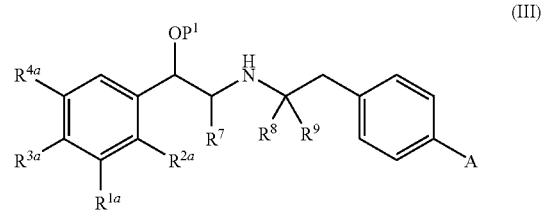

with a compound of formula (IV):

in the presence of a transition metal catalyst; or
(ii) a compound of formula (V):

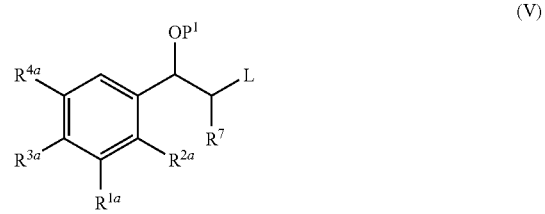

with a compound of formula (VI):

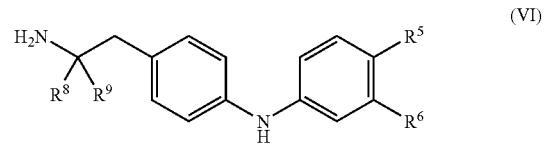

wherein $P^1$ is a hydroxy-protecting group, each of $R^{1a}$, $R^{2a}$, $R^{3a}$, and $R^{4a}$ is independently either defined to be the same as $R^1$, $R^2$, $R^3$, and $R^4$ in formula (I) or is —$OP^2$, wherein $P^2$ is a hydroxy-protecting group; one of A and B is a leaving group and the other of A and B is —$NH_2$; L is a leaving group; and $R^5$, $R^6$, $R^7$, $R^8$, and $R^9$ are defined as in formula (I), to provide a compound of formula (VII);

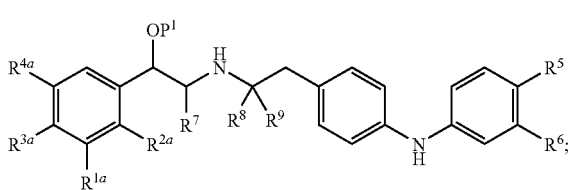

(VII)

(b) removing the protecting group $P^1$ to provide a compound of formula (VIII):

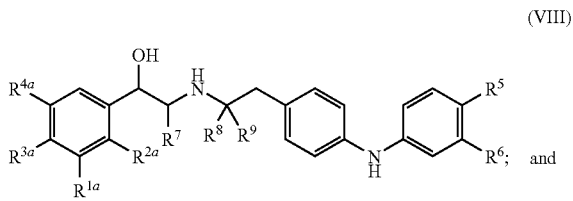

(VIII)

(c) when any of $R^{1a}$, $R^{2a}$, $R^{3a}$, or $R^{4a}$ is —$OP^2$, removing the protecting group $P^2$ to provide a compound of formula (I), or a salt or stereoisomer thereof.

Pharmaceutical Compositions

The invention also provides pharmaceutical compositions comprising a compound of the invention. Accordingly, the compound, preferably in the form of a pharmaceutically-acceptable salt, can be formulated for any suitable form of administration, such as oral or parenteral administration, or administration by inhalation.

By way of illustration, the compound can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. The pharmaceutical compositions may contain common carriers and excipients, such as cornstarch or gelatin, lactose, magnesium sulfate, magnesium stearate, sucrose, microcrystalline cellulose, kaolin, mannitol, dicalcium phosphate, sodium chloride, and alginic acid. Disintegrators commonly used in the formulations of this invention include croscarrnellose, microcrystalline cellulose, cornstarch, sodium starch glycolate and alginic acid.

A liquid composition will generally consist of a suspension or solution of the compound or pharmaceutically-acceptable salt in a suitable liquid carrier(s), for example ethanol, glycerine, sorbitol, non-aqueous solvent such as polyethylene glycol, oils or water, optionally with a suspending agent, a solubilizing agent (such as a cyclodextrin), preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone.

The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically-acceptable salts that are active when given parenterally can be formulated for intramuscular, intrathecal, or intravenous administration.

A typical composition for intra-muscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol; a chelating agent, for example, ethylenediamine tetraacetic acid; a solubilizing agent, for example, a cyclodextrin; and an anti-oxidant, for example, sodium metabisulphite, may be included in the formulation. Alternatively, the solution can be freeze dried and then reconstituted with a suitable solvent just prior to administration.

The compounds of this invention and their pharmaceutically-acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

One preferred manner for administering a compound of the invention is inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Conventional nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 μm.

A typical formulation for use in a conventional nebulizer device is an isotonic aqueous solution of a pharmaceutical salt of the active agent at a concentration of the active agent of between about 0.05 μg/mL and about 1 mg/mL. Suitable nebulizer devices are provided commercially, for example, by PARI GmbH (Starnberg, Germany). Other nebulizer devices have been disclosed, for example, in U.S. Pat. No. 6,123,068.

DPI's typically administer a therapeutic agent in the form of a free flowing powder that can be dispersed in a patient's air-stream during inspiration. Alternative DPI devices which use an external energy source to disperse the powder are also being developed. In order to achieve a free flowing powder, the therapeutic agent can be formulated with a suitable excipient (e.g., lactose or starch). A dry powder formulation can be made, for example, by combining dry lactose particles with micronized particles of a suitable form, typically a pharmaceutically-acceptable salt, of a compound of the invention (i.e. the active agent) and dry blending. Alternatively, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalklanes (HFA), such as 1,1,1,2-tetrafluoroethane (HFA 134a) and 1,1,1,2,3,3,3,-heptafluoro-n-propane, (HFA 227) have been developed. Additional components of HFA formulations for MDI administration include co-solvents, such as ethanol or pentane, and surfactants, such as sorbitan trioleate, oleic acid, lecithin, and glycerin. (See, for example, U.S. Pat. No. 5,225,183, EP 0717987 A2, and WO 92/22286.)

Thus, a suitable formulation for MDI administration can include from about 0.001% to about 2% by weight of the present crystalline form, from about 0% to about 20% by weight ethanol, and from about 0% to about 5% by weight surfactant, with the remainder being the FIFA propellant. In one approach, to prepare the formulation, chilled or pressurized hydrofluoroalkane is added to a vial containing the present crystalline form, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,227.

In an alternative preparation, a suspension formulation is prepared by spray drying a coating of surfactant on micronized particles of a pharmaceutical salt of active compound. (See, for example, WO 99/53901 and WO 00/61108.) For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

It will be understood that any form of the compounds of the invention, (i.e. free base, pharmaceutical salt, or solvate) that is suitable for the particular mode of administration, can be used in the pharmaceutical compositions discussed above.

The active compounds are expected to be effective over a wide dosage range and to be administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 μg/day to about 100 mg/day, preferably 0.5 to 1000 μg/day.

Suitable doses of the therapeutic agents for inhalation administration are in the general range of from about 0.05 μg/day to about 1000 μg/day, preferably from about 0.1 μg/day to about 500 μg/day. It will be understood that the fraction of active agent delivered to the lung characteristic of particular delivery devices is taken into account in determining suitable doses for inhalation administration.

Among other properties, compounds of the invention have been found to be potent and selective agonists of the $\beta_2$ adrenergic receptor. In particular, compounds of the invention demonstrate excellent selectivity for the $\beta_2$ adrenergic receptor as compared with the $\beta_1$ and $\beta_3$ adrenergic receptors. Furthermore, compounds of the invention have been found to possess surprising and unexpected duration of action. As described in the biological assays below, compounds of the invention demonstrated duration of action greater than 24 hours in an animal model of bronchoprotection.

The invention thus provides a method of treating a disease or condition in a mammal associated with $\beta_2$ adrenergic receptor activity, the method comprising administering to the mammal a therapeutically effective amount of a compound of the invention or of a pharmaceutical composition comprising a compound of the invention.

The present active agents can also used as part of a combination comprising, in addition, one or more other therapeutic agents. For example, the present agents can be administered together with one or more therapeutic agents selected from anti-inflammatory agents (e.g. corticosteroids and non-steroidal anti-inflammatory agents (NSAIDs), antichlolinergic agents (particularly muscarinic receptor antagonists), other $\beta_2$ adrenergic receptor agonists, antiinfective agents (e.g. antibiotics or antivirals) or antihistamines. The invention thus provides, in a further aspect, a combination comprising a compound of the invention and one or more therapeutic agents, for example, an anti-inflammatory agent, an antichlolinergic agent, another $\beta_2$ adrenergic receptor agonist, an antiinfective agent or an antihistamine.

The other therapeutic agents can be used in the form of pharmaceutically-acceptable salts or solvates. As appropriate, the other therapeutic agents can be used as optically pure stereoisomers.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16αmethyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1, 4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene -17β-carbothioic acid S-fluoromethyl ester and 6α,9α-difluoro-17α-[(2-furanylcarbonyl) oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. Representative phosphodiesterase-4 (PDE4) inhibitors or mixed PDE3/PDE4 inhibitors include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-cyclopentyloxy)-4-methoxyphenyl]cyclohexane-1-carboxylic acid and the like, or pharmaceutically-acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic a tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically-acceptable salt.

Azelastine hydrochloride is yet another $H_1$ receptor antagonist which may be used in combination with a compound of the invention.

Examples of preferred anti-histamines include methapyrilene and loratadine.

The invention thus provides, in a further aspect, a combination comprising a compound of formula (I) or a pharmaceutically-acceptable salt or solvate or stereoisomer thereof and a corticosteroid. In particular, the invention provides a combination wherein the corticosteroid is fluticasone propionate or wherein the corticosteroid is 6α,9α-difluoro-17α-[(2-furanylcarbonyl)oxy]-11β-hydroxy-16αmethyl-3-oxo-androsta-1,4-diene-17β-carbothioic acid S-fluoromethyl ester or 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

The invention thus provides, in a further aspect, a combination comprising a compound of formula (I) or a pharmaceutically-acceptable salt or solvate or stereoisomer thereof and a PDE4 inhibitor.

The invention thus provides, in a further aspect, a combination comprising a compound of formula (I) or a pharmaceutically-acceptable salt or solvate or stereoisomer thereof and an anticholinergic agent.

The invention thus provides, in a further aspect, a combination comprising a compound of formula (I) or a pharmaceutically-acceptable salt or solvate or stereoisomer thereof and an antihistamine.

The invention thus provides, in a further aspect, a combination comprising a compound of formula (I) or a pharmaceutically-acceptable salt or solvate or stereoisomer thereof together with a PDE4 inhibitor and a corticosteroid.

The invention thus provides, in a further aspect, a combination comprising a compound of formula (I) or a pharmaceutically-acceptable salt or solvate or stereoisomer thereof together with an anticholinergic agent and a corticosteroid.

As used in the above combinations, the term, "a compound of formula (I)" includes a compound of formula (II) and preferred groups thereof, and any individually disclosed compound or compounds.

Accordingly, the pharmaceutical compositions of the invention can optionally comprise combinations of a compound of formula (I) or a pharmaceutically-acceptable salt or solvate or stereoisomer thereof with one or more other therapeutic agents, as described above.

The individual compounds of the combinations of the invention may be formulated separately or formulated together in a single pharmaceutical composition. The individual compounds may be administered either sequentially or simultaneously in separate or combined pharmaceutical formulations. Appropriate doses of known therapeutic agents will be readily appreciated by those skilled in the art. Methods of treatment of the invention, therefore, include administration of the individual compounds of such combinations either sequentially or simultaneously in separate or combined pharmaceutical formulations.

Thus, according to a further aspect, the invention provides a method of treating a disease or condition associated with $\beta_2$ adrenergic receptor activity in a mammal, the method comprising administering to the mammal a therapeutically effective amount of a combination of a compound of formula (I) or a pharmaceutically-acceptable salt or solvate or stereoisomer thereof and one or more other therapeutic agents.

Since compounds of the invention are $\beta_2$ adrenergic receptor agonists, such compounds are also useful as research tools for investigating or studying biological systems or samples having $\beta_2$ adrenergic receptors, or for discovering new $\beta_2$ adrenergic receptor agonists. Moreover, since compounds of the invention exhibit selectivity for $\beta_2$ adrenergic receptors as compared with binding and functional activity at receptors of other β adrenergic subtypes, such compounds are also useful for studying the effects of selective agonism of $\beta_2$ adrenergic receptors in a biological system or sample. Any suitable biological system or sample having $\beta_2$ adrenergic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like.

A biological system or sample comprising a $\beta_2$ adrenergic receptor is contacted with a $\beta_2$ adrenergic receptor-agonizing amount of a compound of the invention. The effects of agonizing the $\beta_2$ adrenergic receptor are determined using conventional procedures and equipment, such as radioligand binding assays and functional assays, for example the assay for ligand-mediated changes in intracellular cyclic adenosine monophosphate (cAMP) described below, or assays of a similar nature. A $\beta_2$ adrenergic receptor-agonizing amount of a compound of the invention will typically range from about 1 nanomolar to about 1000 nanomolar. When compounds of the invention are used as research tools for discovering new $\beta_2$ adrenergic receptor agonists, the invention also includes, as separate embodiments, both the generation of comparison data (using the appropriate assays) and the analysis of the test data to identify test compounds of interest.

The following non-limiting examples illustrate representative pharmaceutical compositions of the invention. Additional suitable carriers for formulations of the active compounds of the present invention can be found in *Remington: The Science and Practice of Pharmacy*, 20th Edition, Lippincott Williams & Wilkins, Philadelphia, Pa., 2000.

Formulation Example A

This example illustrates the preparation of a representative pharmaceutical composition for oral administration of a compound of this invention:

| Ingredients | Quantity per tablet, (mg) |
|---|---|
| Active Compound | 1 |
| Lactose, spray-dried | 148 |
| Magnesium stearate | 2 |

The above ingredients are mixed and introduced into a hard-shell gelatin capsule.

Formulation Example B

This example illustrates the preparation of another representative pharmaceutical composition for oral administration of a compound of this invention:

| Ingredients | Quantity per tablet, (mg) |
|---|---|
| Active Compound | 1 |
| Cornstarch | 50 |
| Lactose | 145 |
| Magnesium stearate | 5 |

The above ingredients are mixed intimately and pressed into single scored tablets.

Formulation Example C

This example illustrates the preparation of a representative pharmaceutical composition for oral administration of a compound of this invention.

An oral suspension is prepared having the following composition.

| Ingredients | |
|---|---|
| Active Compound | 3 mg |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

Formulation Example D

This example illustrates the preparation of a representative pharmaceutical composition containing a compound of this invention.

An injectable preparation buffered to a pH of 4 is prepared having the following composition:

| Ingredients | |
|---|---|
| Active Compound | 0.1 mg |
| Sodium Acetate Buffer Solution (0.4 M) | 2.0 mL |
| HCl (1N) | q.s. to pH 4 |
| Water (distilled, sterile) | q.s. to 20 mL |

Formulation Example E

This example illustrates the preparation of a representative pharmaceutical composition for injection of a compound of this invention.

A reconstituted solution is prepared by adding 20 mL of sterile water to 1 mg of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

Formulation Example F

This example illustrates the preparation of a representative pharmaceutical composition for topical application of a compound of this invention.

| Ingredients | grams |
|---|---|
| Active compound | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Formulation Example G

This example illustrates the preparation of a representative pharmaceutical composition containing a compound of the invention.

An aqueous aerosol formulation for use in a nebulizer is prepared by dissolving 0.1 mg of a pharmaceutical salt of active compound in a 0.9% sodium chloride solution acidified with citric acid. The mixture is stirred and sonicated until the active salt is dissolved. The pH of the solution is adjusted to a value in the range of from 3 to 8 by the slow addition of NaOH.

Formulation Example H

This example illustrates the preparation of a dry powder formulation containing a compound of the invention for use in inhalation cartridges.

Gelatin inhalation cartridges are filled with a pharmaceutical composition having the following ingredients:

| Ingredients | mg/cartridge |
|---|---|
| Pharmaceutical salt of active compound | 0.2 |
| Lactose | 25 |

The pharmaceutical salt of active compound is micronized prior to blending with lactose. The contents of the cartridges are administered using a powder inhaler.

Formulation Example I

This example illustrates the preparation of a dry powder formulation containing a compound of the invention for use in a dry powder inhalation device.

A pharmaceutical composition is prepared having a bulk formulation ratio of micronized pharmaceutical salt to lactose of 1:200. The composition is packed into a dry powder inhalation device capable of delivering between about 10 μg and about 100 μg of active drug ingredient per dose.

Formulation Example J

This example illustrates the preparation of a formulation containing a compound of the invention for use in a metered dose inhaler.

A suspension containing 5% pharmaceutical salt of active compound, 0.5% lecithin, and 0.5% trehalose is prepared by dispersing 5 g of active compound as micronized particles with mean size less than 10 µm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

Formulation Example K

This example illustrates the preparation of a formulation containing a compound of the invention for use in a metered dose inhaler.

A suspension containing 5% pharmaceutical salt of active compound and 0.1% lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into canisters with pressurized 1,1,1,2,3,3,3-heptafluoro-n-propane.

Biological Assays

The compounds of this invention, and their pharmaceutically-acceptable salts, exhibit biological activity and are useful for medical treatment. The ability of a compound to bind to the $\beta_2$ adrenergic receptor, as well as its selectivity, agonist potency, and intrinsic activity can be demonstrated using Tests A-B below, or can be demonstrated using other tests that are known in the art.

Abbreviations

% Eff % efficacy
ATCC American Type Culture Collection
BSA Bovine Serum Albumin
cAMP Adenosine 3':5'-cyclic monophosphate
DMEM Dulbecco's Modified Eagle's Medium
DMSO Dimethyl sulfoxide
EDTA Ethylenediaminetetraacetic acid
Emax maximal efficacy
FBS Fetal bovine serum
Gly Glycine
HEK-293 Human embryonic kidney-293
PBS Phosphate buffered saline
rpm rotations per minute
Tris Tris(hydroxymethyl)aminomethane Membrane Preparation from Cells Expressing Human $\beta_1$ or $\beta_2$ Adrenergic Receptors HEK-293 derived cell lines stably expressing cloned human $\beta_1$ or $\beta_2$ adrenergic receptors, respectively, were grown to near confluency in DMEM with 10% dialyzed FBS in the presence of 500 μg/mL Geneticin. The cell monolayer was lifted with Versene 1:5,000 (0.2 g/L EDTA in PBS) using a cell scraper. Cells were pelleted by centrifugation at 1,000 rpm, and cell pellets were either stored frozen at −80° C. or membranes were prepared immediately. For preparation, cell pellets were resuspended in lysis buffer (10 mM Tris/HCL pH 7.4 @4° C., one tablet of "Complete Protease Inhibitor Cocktail Tablets with 2 mM EDTA" per 50 mL buffer (Roche cat. #1697498, Roche Molecular Biochemicals, Indianapolis, Ind.)) and homogenized using a tight-fitting Dounce glass homogenizer (20 strokes) on ice. The homogenate was centrifuged at 20,000×g, the pellet was washed once with lysis buffer by resuspension and centrifugation as above. The final pellet was resuspended in membrane buffer (75 mM Tris/HCl pH 7.4, 12.5 mM $MgCl_2$, 1 mM EDTA @25° C.). Protein concentration of the membrane suspension was determined by the method of Bradford (Bradford M M., *Analytical Biochemistry,* 1976, 72, 248-54). Membranes were stored frozen in aliquots at −80° C.

Test A

Radioligand Binding Assay on Human $\beta_1$ and $\beta_2$ Adrenergic Receptors

Binding assays were performed in 96-well microtiter plates in a total assay volume of 100 μL with 5 μg membrane protein for membranes containing the human $\beta_2$ adrenergic receptor, or 2.5 μg membrane protein for membranes containing the human $\mu_1$ adrenergic receptor in assay buffer (75 mM Tris/HCl pH 7.4 @25° C., 12.5 mM $MgCl_2$, 1 mM EDTA, 0.2% BSA). Saturation binding studies for determination of $K_d$ values of the radioligand were done using [$^3$H]dihydroalprenolol (NET-720, 100 Ci/mmol, PerkinElmer Life Sciences Inc., Boston, Mass.) at 10 different concentrations ranging from 0.01 nM-200 nM. Displacement assays for determination of $pK_i$ values of compounds were done with [$^3$H]dihydroalprenolol at 1 nM and 10 different concentrations of compound ranging from 40 pM-10 μM. Compounds were dissolved to a concentration of 10 mM in dissolving buffer (25 mM Gly-HCl pH 3.0 with 50% DMSO), then diluted to 1 mM in 50 mM Gly-HCl pH 3.0, and from there serially diluted into assay buffer. Non-specific binding was determined in the presence of 10 μM unlabeled alprenolol. Assays were incubated for 90 minutes at room temperature, binding reactions were terminated by rapid filtration over GF/B glass fiber filter plates (Packard BioScience Co., Meriden, Conn.) presoaked in 0.3% polyethyleneimine. Filter plates were washed three times with filtration buffer (75 mM Tris/HCl pH 7.4 @4° C., 12.5 mM $MgCl_2$, 1 mM EDTA) to remove unbound radioactivity. Plates were dried, 50 μL Microscint-20 liquid scintillation fluid (Packard BioScience Co., Meriden, Conn.) was added and plates were counted in a Packard Topcount liquid scintillation counter (Packard BioScience Co., Meriden, Conn.). Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 μM alprenolol. $K_i$ values for compounds were calculated from observed $IC_{50}$ values and the $K_d$ value of the radioligand using the Cheng-Prusoff equation (Cheng Y, and Prusoff W H., *Biochemical Pharmacology,* 1973, 22, 23, 3099-108). The receptor subtype selectivity was calculated as the ratio of $K_i(\beta_1)/K_i(\beta_2)$. Compounds of the invention demonstrated greater binding at the $\beta_2$ adrenergic receptor than at the $\beta_1$ adrenergic receptor, i.e. $K_i(\beta_1)>K_i(\beta_2)$ with selectivity greater than about 30.

Test B

Whole-cell cAMP Flashplate Assays with Cell Lines Heterologously Expressing Human $\beta_1$ Adrenoceptor, $\beta_2$ Adrenoceptor, and $\beta_3$ Adrenoceptor, Respectively A HEK-293 cell line stably expressing cloned human $\beta_1$ adrenergic receptor (clone H34.1) was grown to about 70%-90% confluency in medium consisting of DMEM supplemented with 10% FBS and 500 μg/mL Geneticin. A HEK-293 cell line stably expressing cloned human $\beta_2$-adrenoceptor (clone H24.14) was grown in the same medium to full confluency. A CHO-K1 cell line stably expressing cloned human $\beta_3$-adrenoceptor was grown to about 70%-90% confluency in Ham's F-12 medium supplemented with 10% FBS and with 800 μg/mL Geneticin added to every fifth passage. The day before the assay, cultures were switched to the same growth-media without antibiotics.

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed once with PBS, lifted with Versene 1:5,000 (0.2 g/L EDTA in PBS) and counted. Cells were pelleted by centrifugation at 1,000 rpm and resuspended in stimulation buffer prewarmed to 37° C. For cells expressing the $\beta_1$-adrenoceptor, 10 nM ICI 118,551 were added to the stimulation buffer, and cells were incubated for 10 mM at 37° C. Cells were used at final concentrations of 30,000, 40,000 and 70,000 cells/well for the $\beta_1$-adrenoceptor-, the $\beta_2$-adrenoceptor- and the $\beta_3$-adrenoceptor expressing cells, respectively. Compounds were dissolved to a concentration of 10 mM in DMSO, then diluted to 1 mM in 50 mM Gly-HCl pH 3.0, and from there serially diluted into assay buffer (75 mM Tris/HCl pH 7.4 @25° C., 12.5 mM $MgCl_2$, 1 mM EDTA, 0.2% BSA). Compounds were tested in the assay at 11 different concentrations, ranging from 10 μM to 9.5 pM. Reactions were incubated for 10 min at 37° C. and stopped by addition of 100 μl ice-cold detection buffer. Plates were sealed, incubated over night at 4° C. and counted the next morning in a topcount scintillation counter (Packard BioScience Co., Meriden, Conn.). The amount of cAMP produced per mL of reaction was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the 3-parameter model for sigmoidal dose-response (Hill slope=1). Agonist potencies were expressed as $pEC_{50}$ values.

Compounds of the invention demonstrated potent activity at the $\beta_2$ adrenergic receptor in this assay, as evidenced by $pEC_{50}$ values greater than about 9. In addition, the compounds tested demonstrated selectivity in functional activity at the $\beta_2$ receptor as compared with functional activity at the $\beta_1$ and $\beta_3$ receptors. In particular, compounds of the invention demonstrated $EC_{50}(\beta_1)/EC_{50}(\beta_2)$ ratios of greater than about 10 and $EC_{50}(\beta_3)/EC_{50}(\beta_2)$ ratios of greater than about 50.

Test C

Whole-Cell cAMP Flashplate Assay With a Lung Epithelial Cell Line Endogenously Expressing Human $\beta_2$ Adrenergic Receptor For the determination of agonist potencies and efficacies (intrinsic activities) in a cell line expressing endogenous levels of $\beta_2$ adrenergic receptor, a human lung epithelial cell line (BEAS-2B) was used (ATCC CRL-9609, American Type Culture Collection, Manassas, Va.) (January B, et al., *British Journal of Pharmacology*, 1998, 123, 4, 701-11). Cells were grown to 75-90% confluency in complete, serum-free medium (LHC-9 MEDIUM containing Epinephrine and Retinoic Acid, cat #181-500, Biosource International, Camarillo, Calif.). The day before the assay, medium was switched to LHC-8 (No epinephrine or retinoic acid, cat #141-500, Biosource International, Camarillo, Calif.).

cAMP assays were performed in a radioimmunoassay format using the Flashplate Adenylyl Cyclase Activation Assay System with $^{125}$I-cAMP (NEN SMP004, PerkinElmer Life Sciences Inc., Boston, Mass.), according to the manufacturers instructions.

On the day of the assay, cells were rinsed with PBS, lifted by scraping with 5 mM EDTA in PBS, and counted. Cells were pelleted by centrifugation at 1,000 rpm and resuspended in stimulation buffer prewarmed to 37° C. at a final concentration of 600,000 cells/mL. Cells were used at a final concentration of 30,000 cells/well in the assay. Compounds were dissolved to a concentration of 10 mM in dissolving buffer (25 mM Gly-HCl pH 3.0 with 50% DMSO), then diluted to 1 mM in 50 mM. Gly-HCl pH 3.0, and from there serially diluted into assay buffer (75 mM Tris/HCl pH 7.4 @25° C., 12.5 mM $MgCl_2$, 1 mM EDTA, 0.2% BSA).

Compounds were tested in the assay at 10 different concentrations, ranging from 10 μM to 40 pM. Maximal response was determined in the presence of 10 μM Isoproterenol. Reactions were incubated for 10 mM at 37° C. and stopped by addition of 100 μl ice-cold detection buffer. Plates were sealed, incubated over night at 4° C. and counted the next morning in a topcount scintillation counter (Packard Bio-Science Co., Meriden, Conn.). The amount of cAMP produced per mL of reaction was calculated based on the counts observed for samples and cAMP standards, as described in the manufacturer's user manual. Data were analyzed by non-linear regression analysis with the GraphPad Prism Software package (GraphPad Software, Inc., San Diego, Calif.) using the 4-parameter model for sigmoidal dose-response with variable slope. Compounds of the invention tested in this assay demonstrated $pEC_{50}$ values greater than about 8.

Compound efficacy (% Eff) was calculated from the ratio of the observed Emax (TOP of the fitted curve) and the maximal response obtained for 10 μM isoproterenol and was expressed as % Eff relative to isoproterenol. The compounds tested demonstrated a % Eff greater than about 50.

Test D

Assay of Bronchoprotection Against Acetylcholine-Induced Bronchospasm in a Guinea Pig Model Groups of 6 male guinea pigs (Duncan-Hartley (HsdPoc: DH) Harlan, Madison, Wis.) weighing between 250 and 350 g were individually identified by cage cards. Throughout the study animals were allowed access to food and water ad libitum.

Test compounds were administered via inhalation over 10 minutes in a whole-body exposure dosing chamber (R&S Molds, San Carlos, Calif.). The dosing chambers were arranged so that an aerosol was simultaneously delivered to 6 individual chambers from a central manifold. Following a 60 minute acclimation period and a 10 minute exposure to nebulized water for injection (WFI), guinea pigs were exposed to an aerosol of test compound or vehicle (WFI). These aerosols were generated from aqueous solutions using an LC Star Nebulizer Set (Model 22F51, PARI Respiratory Equipment, Inc. Midlothian, Va.) driven by a mixture of gases ($CO_2$=5%, $O_2$=21% and $N_2$=74%) at a pressure of 22 psi. The gas flow through the nebulizer at this operating pressure was approximately 3 L/minute. The generated aerosols were driven into the chambers by positive pressure. No dilution air was used during the delivery of aerosolized solutions. During the 10 minute nebulization, approximately 1.8 mL of solution was nebulized. This was measured gravimetrically by comparing pre-and post-nebulization weights of the filled nebulizer.

The bronchoprotective effects of compounds administered via inhalation were evaluated using whole body plethysmography at 1.5, 24, 48 and 72 hours post-dose. Forty-five minutes prior to the start of the pulmonary evaluation, each guinea pig was anesthetized with an intramuscular injection of ketamine (43.75 mg/kg), xylazine (3.50 mg/kg) and acepromazine (1.05 mg/kg). After the surgical site was shaved and cleaned with 70% alcohol, a 2-5 cm midline incision of the ventral aspect of the neck was made. Then, the jugular vein was isolated and cannulated with a saline-filled polyethylene catheter (PE-50, Becton Dickinson, Sparks, Md.) to allow for intravenous infusions of a 0.1 mg/mL solution of acetylcholine (Ach), (Sigma-Aldrich, St. Louis, Mo.) in saline. The trachea was then dissected free and cannulated with a 14G teflon tube (#NE-014, Small Parts, Miami Lakes, Fla.). If required, anesthesia was maintained by additional intramuscular injections of the aforementioned anesthetic cocktail. The depth of anesthesia was monitored and adjusted if the animal responded to pinching of its paw or if the respiration rate was greater than 100 breaths/minute.

Once the cannulations were complete, the animal was placed into a plethysmograph (#PLY3114, Buxco Electronics, Inc., Sharon, Conn.) and an esophageal pressure cannula was inserted to measure pulmonary driving pressure (pressure). The teflon tracheal tube was attached to the opening of the plethysmograph to allow the guinea pig to breathe room air from outside the chamber. The chamber was then sealed. A heating lamp was used to maintain body temperature and the guinea pig's lungs were inflated 3 times with 4 mL of air using a 10 mL calibration syringe (#5520 Series, Hans Rudolph, Kansas City, Mo.) to ensure that the lower airways had not collapsed and that the animal did not suffer from hyperventilation.

Once it was determined that baseline values were within the range 0.3-0.9 mL/cm $H_2O$ for compliance and within the range 0.1-0.199 cm $H_2O$/mL per second for resistance, the pulmonary evaluation was initiated. A Buxco pulmonary measurement computer program enabled the collection and derivation of pulmonary values. Starting this program initiated the experimental protocol and data collection. The changes in volume over time that occurred within the plethysmograph with each breath were measured via a Buxco pressure transducer. By integrating this signal over time, a measurement of flow was calculated for each breath. This signal, together with the pulmonary driving pressure changes, which were collected using a Sensym pressure transducer (#TRD4100), was connected via a Buxco (MAX 2270) preamplifier to a data collection interface (#'s SFT3400 and SFT3813). All other pulmonary parameters were derived from these two inputs.

Baseline values were collected for 5 minutes, after which time the guinea pigs were challenged with Ach. Ach was infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. If resistance or compliance had not returned to baseline values at 3 minutes following each Ach dose, the guinea pig's lungs were inflated 3 times with 4 mL of air from a 10 mL calibration syringe. Recorded pulmonary parameters included respiration frequency (breaths/minute), compliance (mL/cm $H_2O$) and pulmonary resistance (cm $H_2O$/mL per second) (Giles et al., 1971). Once the pulmonary function measurements were completed at minute 35 of this protocol, the guinea pig was removed from the plethysmograph and euthanized by $CO_2$ asphyxiation.

The quantity $PD_2$, which is defined as the amount of Ach needed to cause a doubling of the baseline pulmonary resistance, was calculated using the pulmonary resistance values derived from the flow and the pressure over a range of Ach challenges using the following equation. This was derived from the equation used to calculate $PC_{20}$ values in the clinic (Am. Thoracic Soc, 2000).

$$PD_2 = \mathrm{antilog}\left[\log C_1 + \frac{(\log C_2 - \log C_1)(2R_0 - R_1)}{R_2 - R_1}\right]$$

where:

$C_1$=Second to last Ach concentration (concentration preceding $C_2$)

$C_2$=Final concentration of Ach (concentration resulting in a 2-fold increase in pulmonary resistance ($R_L$))

$R_0$=Baseline $R_L$ value $R_1$=$R_L$ value after $C_1$ $R_2$=$R_L$ value after $C_2$ Statistical analysis of the data was performed using a One-Way Analysis of Variance followed by post-hoc analysis using a Bonferroni/Dunn test. A P-value<0.05 was considered significant.

Dose-response curves were fitted with a four parameter logistic equation using GraphPad Prism, version 3.00 for Windows (GraphPad Software, San Diego, Calif.)

$Y$=Min+(Max−Min)/(1+10^((log $ED_{50}$−$X$)* Hillslope)), where X is the logarithm of dose, Y is the response ($PD_2$), and Y starts at Min and approaches asymptotically to Max with a sigmoidal shape.

Representative compounds of the invention were found to have significant bronchoprotective activity at time points beyond 24 hours post-dose.

The following synthetic examples are offered to illustrate the invention, and are not to be construed in any way as limiting the scope of the invention.

EXAMPLES

General: Unless noted otherwise, reagents, starting material and solvents were purchased from commercial suppliers, for example Sigma-Aldrich (St. Louis, Mo.), J. T. Baker (Phillipsburg, N.J.), and Honeywell Burdick and Jackson (Muskegon, Mich.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by preparative HPLC using the general protocol described below; NMR samples were dissolved in deuterated solvent ($CD_3OD$, $CDCl_3$, or DMSO-d6), and spectra were acquired with a Varian Gemini 2000 instrument (300 MHz) under standard parameters; and mass spectrometric identification was performed by an electrospray ionization method (ESMS) with a Perkin Elmer instrument (PE SCIEX API 150 EX).

Example 1

Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one a. Preparation of 4-(2-amino-2-methyl-propoxy)-phenylamine hydrochloride

A vigorously stirred slurry of sodium hydride (60% dispersion in mineral oil, 11.32 g, 0.28 mol) in dimethylsulfoxide (400 mL) was heated at 45° C. for 1 h. To this slurry was then added neat 2-amino-2-methyl-1-propanol (25.3 g, 1 equiv). The reaction mixture was warmed to 75° C. for 1 h then cooled to 20° C. in an ice bath. 1-Fluoro-4-nitrobenzene (40 g, 1 equiv) was added slowly, maintaining the temperature below 30° C., and the resulting dark red solution was stirred at room temperature for a further 1 h. The reaction was quenched with water (1000 mL), extracted with dichloromethane (500 mL), and the organic layer washed (1:1 saturated aqueous sodium chloride:water, 1000 mL). The product was precipitated by addition of 3M hydrochloric acid (400 mL) to the organic layer. The resulting orange solid was then filtered and washed with dichloromethane until the filtrate was colorless.

The solid material was immediately transferred to a hydrogenation flask. Palladium (10% w/w on carbon, 50% w/w water) was added, followed by methanol (500 mL). The slurry was shaken vigorously under 3 atmospheres of hydrogen gas for 16 h. The catalyst was then filtered, the solvent removed under reduced pressure, and the resulting solid dried by azeotroping with toluene (3×150 mL) to afford the title intermediate as a white solid (40 g, 0.18 mol, 65%.

b. Preparation of 5-[(R)-2-(2-{4-[4-(2-amino-2-methyl-propoxy)-phenylamino]-phenyl}-ethylamino)-1-(tert-butyl-dimethyl-silanyloxy)-ethyl]-8-benzyloxy-1H-quinolin-2-one A mixture of the product of step a (23.2 g, 1.1 equiv), 8-benzyloxy-5-{(R)-2-[2-(4-bromo-phenyl)-ethylamino-1-(tert-butyl-dimethyl-silanyloxy)-ethyl}-1H-quinolin-2-one hydrochloride (66.0 g, 0.1 mol), and sodium tert-butoxide (54.0 g, 5.5 equiv) in toluene (600 mL) was stirred at 90° C. until a homogenous solution was obtained. Palladium tris (dibenzylideneacetone) (1.4 g, 0.015 equiv) was added, followed by rac-2,2'-bis(diphenylphosphino)-1,1'-binapthyl (2.87 g, 0.045 equiv). The reaction mixture was stirred at 90° C. for 3 h, then allowed to cool. The solution was washed with water (100 mL), 1:1 saturated aqueous sodium chloride:water (100 mL), then dried over sodium sulfate. The solvent was removed under reduced pressure to afford the title intermediate as a dark brown solid (40 g crude), which was used without further purification.

c. Preparation of 5-[(R)-2-(2-{4-[4-(2-amino-2-methyl-propoxy)-phenylamino]-phenyl}-ethylamino)-1-hydroxy-ethyl]-8-benzyloxy-1H-quinolin-2-one The product of the previous step was treated with triethylamine trihydrofluoride (36 g) in 2-propanol (500 mL)/ethanol (100 mL) at room temperature for 16 h. The mixture was concentrated under reduced pressure to one third of its original volume. 1M aqueous sodium hydroxide (500 mL) was added, followed by acetonitrile (500 mL) and isopropyl acetate (500 mL). The aqueous layer was removed and the organic phase washed with 1:1 saturated aqueous sodium chloride:water (400 mL) then saturated aqueous sodium chloride (400 mL). The organics were dried over sodium sulfate and the solvent removed in vacuo to afford the title intermediate (50 g crude) as a brown solid, which was used without further purification.

d. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one Palladium hydroxide (10 g, 20% w/w on carbon, 50% w/w water) was added to the product from the previous reaction, followed by ethanol (500 mL). The slurry was stirred vigorously under an atmosphere of hydrogen gas for 8 h. The catalyst was filtered and the filtrate concentrated under reduced pressure to afford the title compound (40 g), which was purified by reverse phase HPLC and isolated as its trifluoroacetate salt by lyophilization. $^1$H NMR (300 MHz, DMSO-$d_6$): 10.4 (s, 1H), 9.3 (br s, 1H), 8.7 (br s, 1H), 8.15 (m, 2H), 7.8 (br s, 1H), 7.03 (d, 1H, J=8.2), 6.76-7.01 (m, 10H), 6.42 (d, 1H, J=9.6), 6.1 (br s, 1H), 5.33 (d, 1H, J=9.1), 3.8 (s, 2H), 2.7-3.1 (m, 6H), 1.21 (s, 6H); m/z: [M+H$^+$] calcd for $C_{29}H_{34}N_4O_4$, 503.3; found 503.5.

Examples 2-8

Synthesis of Compounds 2-8

Using procedures similar to those described in Example 1, except replacing the 2-amino-2-methyl-1-propanol with the appropriate alcohol in step a, trifluoroacetate salts of compounds 2-8 were prepared.

Compound 2: 5-[(R)-2-(2-{4-[4-(2-amino-ethoxy)-phenylamino]-phenyl}-ethylamino)-1-hydroxy-ethyl]-8-hydroxy-1H-quinolin-2-one: m/z: [M+H$^+$] calcd for $C_{27}H_{31}N_4O_4$, 475.2; found 475.3.

Compound 3: 5-[(R)-2-(2-{4-[4-(3-amino-propoxy)-phenylamino]-phenyl}-ethylamino)-1-hydroxy-ethyl]-8-hydroxy-1H-quinolin-2-one: m/z: [M+H$^+$] calcd for $C_{28}H_{33}N_4O_4$, 489.2; found 489.5.

Compound 4: 5-[(R)-2-(2-{4-[4-(4-amino-butoxy)-phenylamino]-phenyl}-ethylamino)-1-hydroxy-ethyl]-8-hydroxy-1H-quinolin-2-one: m/z: [M+H$^+$] calcd for $C_{29}H_{35}N_4O_4$, 503.3; found 503.5.

Compound 5: 5-{(R)-2-[2-(4-{4-[2-(2-amino-ethoxy)-ethoxy]-phenylamino}-phenyl)-ethylamino]-1-hydroxy-ethyl}-8-hydroxy-1H-quinolin-2-one: m/z: [M+H$^+$] calcd for $C_{29}H_{35}N_4O_5$, 519.3; found 519.5.

Compound 6: 8-hydroxy-5-[(R)-1-hydroxy-2-(2-{4-[4-(2-morpholin-4-yl-ethoxy)-phenylamino]-phenyl}-ethylamino)-ethyl]-1H-quinolin-2-one: m/z: [M+H$^+$] calcd for $C_{31}H_{37}N_4O_5$, 545.3; found 545.6.

Compound 7: 8-hydroxy-5-[(R)-1-hydroxy-2-(2-{4-[4-(2-piperazin-1-yl-ethoxy)-phenylamino]-phenyl}-ethylamino)-ethyl]-1H-quinolin-2-one: m/z: [M+H$^+$] calcd for $C_{31}H_{38}N_5O_4$, 544.7; found 544.7.

Compound 8: 8-hydroxy-5-[(R)-1-hydroxy-2-(2-{4-[4-(2-pyridin-2-ylmethoxy)-phenylamino]-phenyl}-ethylamino)-ethyl]-1H-quinolin-2-one: m/z: [M+H$^+$] calcd for $C_{31}H_{31}N_4O_4$, 523.1; found 523.2.

Example 9

Synthesis of 5-[(R)-2-(2-{4-[4-(2-amino-2-methyl-propoxy)-3-trifluoromethyl-phenylamino]-phenyl}-ethylamino)-1-hydroxy-ethyl]-8-hydroxy-1H-quinolin-2-one Using procedures similar to those described for Example 1, except replacing the 1-fluoro-4-nitrobenzene with 1-fluoro- 4-nitro-2-trifluoromethylbenzene in step a, the title compound was prepared. m/z: [M+H$^+$] calcd for $C_{30}H_{34}F_3N_4O_4$, 571.3; found 571.3.

Example 10

Synthesis of 8-hydroxy-5-{(R)-1-hydroxy-2-[2-(4-{4-[2-(4-methanesulfonyl-piperazin-1-yl)-ethoxy]-phenylamino}-phenyl)-ethylamino]-ethyl}-1H-quinolin-2-one a. Preparation of 8-benzyloxy-5-[(R)-1-(tert-butyl-dimethyl-silanyloxy) -2-(2-{4-[4-(2-piperazin-1-yl-ethoxy)-phenylamino]-phenyl}-ethylamino)-ethyl]-1H-quinolin-2-one Using procedures similar to those described for Example 1, steps a and b, except replacing the 2-amino-2-methyl-1-propanol with N-(2-hydroxyethyl)piperazine in step a, the title intermediate was prepared.

b. Preparation of 8-benzyloxy-5-{(R)-1-(tert-butyl-dimethyl-silanyloxy) -2-[2-(4-{4-[2-(4-methane-sulfonyl-piperazin-1-yl)-ethoxy]-phenylamino}-phenyl)-ethylamino]-ethyl}-1H-quinolin-2-one The product of step a (100 mg) was treated with methanesulfonyl chloride (15.3 mg, 1 equiv) in a mixture of diisopropylethylamine (0.14 mL) and tetrahydrofuran (2 mL) at room temperature for 1 h. The mixture was then evaporated to yield the title intermediate.

c. Synthesis of 8-hydroxy-5-{(R)-1-hydroxy-2-[2-(4-{4-[2-(4-methanesulfonyl-piperazin-1-yl)-ethoxy]-phenylamino}-phenyl)-ethylamino]-ethyl}-1H-quinolin-2-one Using procedures similar to those described for Example 1, steps c and d, the intermediate of step b was transformed to the title compound. m/z: [M+H$^+$]calcd for $C_{32}H_{40}N_5O_6S$, 622.3; found 622.5.

Example 11

Synthesis of 5-1-[(R)-2-(2-{4-[4-(2-amino -ethyl)-phenylamino]-phenyl}-ethylamino)-1-hydroxy-ethyl]-8-hydroxy-1H-quinolin-2-one a. Preparation of 5-[(R)-2-(2-{4-[4-(2-amino -ethyl)-phenylamino]-phenyl}-ethylamino)-1-(tert-butyl-dimethyl-silanyloxy)-ethyl]-8-benzyloxy-1H-quinolin-2-one Tris(dibenzylideneacetone)dipalladium(0) (0.028 g, 0.031 mmol), followed by rac-2,2'-bis(diphenylphosphino)-1,1'-binapthyl (0.057 g, 0.092 mmol) was added to a solution of 2-(4-aminophenyl)ethylamine (0.100 g, 0.740 mmol), 8-benzyloxy-5-{(R)-2-[2-(4-bromo-phenyl)-ethylamino-1-(tert-butyl-dimethyl-silanyloxy)-ethyl}-1H-quinolin-2-one hydrochloride (0.393 g, 0.612 mmol), and sodium tert-butoxide (0.265 g, 2.75 mmol) in toluene (20 mL) at room temperature. The resulting mixture was heated at 90° C. for 2 h, then allowed to cool. The solution was washed with water (100 mL), 1:1 saturated aqueous sodium chloride:water (100 mL), then dried over magnesium sulfate. The solvent was removed at reduced pressure to afford the title intermediate as a dark brown solid (0.473 g), which was used without further purification.

b. Preparation of 5-[(R)-2-(2-{4-[4-(2-amino -ethyl)-phenylamino]-phenyl}-ethylamino)-1-hydroxy-ethyl]-8-benzyloxy-1H-quinolin-2-one The product of the previous step (0.473 g, 0.714 mmol) was treated with triethylamine trihydrofluoride (0.173 g, 1.07 mmol) in tetrahydrofuran (20 mL) at room temperature for 16 h. The mixture was diluted with dichloromethane (100 mL) and water (100 mL). The resulting mixture was stirred vigorously and made basic (pH>10) by the addition of 1N aqueous sodium hydroxide. The organic phase was washed with water (200 mL) and then washed with saturated aqueous sodium chloride (200 mL). The organics were dried over magnesium sulfate and the solvent removed at reduced pressure to afford the title intermediate (0.500 g) as a brown solid, which was used without further purification.

c. Synthesis of 5-[(R)-2-(2-{4-[4-(2-amino-ethyl) -phenylamino]-phenyl}-ethylamino)-1-hydroxy-ethyl]-8-hydroxy-1H-quinolin-2-one Palladium (0.100 g, 10% wt. on activated carbon) was added to a solution of the product of the previous step in 1:1 methanol:dichloromethane (20 mL). The slurry was stirred vigorously under 1 atmosphere of hydrogen for 16 h. The reaction mixture was filtered through celite and concentrated at reduced pressure to afford the title compound, which was purified by reverse phase HPLC and isolated as its trifluoroacetate salt by lyophilization. $^1$H NMR (300 MHz, DMSO-d$_6$): δ 10.4 (d, 2H), 8.6 (br s, 2H), 8.0 (d, 2H), 7.7 (br s, 3H), 7.0 (d, 1H), 6.96 (d, 4H), 6.84-6.88 (m, 4H), 6.45 (d, 1H), 6.08 (s, 1H), 5.19 (d, 1H), 3.0-3.2 (m, 2H), 2.8 (br s, 2H), 2.72-2.75 (m, 2H), 2.62 (m, 2H); m/z: [M+H$^+$] calcd for $C_{27}H_{30}N_4O_3$, 458.56; found 459.4.

Example 12

Synthesis of 5-[(R)-2-(2-{4-[4-(2-dimethylamino -ethyl)-phenylamino]-phenyl}-ethylamino)-1-hydroxy-ethyl]-8-hydroxy-1H-quinolin-2-one a. Preparation of dimethyl-[2-(4-nitro-phenyl)-ethyl]-amine Dimethylamine hydrochloride (0.390 g, 4.78 mmol) was added to a solution containing 4-nitrophenethyl bromide (1.0 g, 4.35 mmol) and N, N-diisopropylethyamine (1.69 g, 13.05 mmol) in anhydrous dimethylformamide (20 mL). The reaction mixture was heated to 60° C. for 5 hours, then allowed to cool. The solution was diluted with 1:1 water:dichloromethane (200 mL), then added to a separatory funnel. The organics were collected and the product was extracted with 1N aqueous hydrogen chloride. The organics were removed and the aqueous layer was made basic with 1N aqueous sodium hydroxide. The product was extracted with dichloromethane (100 mL) and washed with saturated aqueous sodium chloride (200 mL). The organics were dried over magnesium sulfate and the solvent removed at reduced pressure to afford the title intermediate (0.426 g crude) as a clear oil, which was used without further purification.

b. Preparation of 4-(2-dimethylamino-ethyl)-phenylamine

Palladium (0.043 g, 10% wt. on activated carbon) was added to a solution of the product of the previous step (0.430 g, 2.2 mmol) in methanol (20 mL). The slurry was stirred vigorously under a hydrogen atmosphere for 6 hours. The reaction mixture was filtered and the filtrate concentrated at reduced pressure to afford the title intermediate (0.307 g crude) which was used without further purification.

c. Synthesis of 5-[(R)-2-(2-{4-[4-(2-dimethylamino-ethyl)-phenylamino]-phenyl}-ethylamino)-1-hydroxy-ethyl]-8-hydroxy-1H-quinolin-2-one Using procedures similar to those described for Example 11, except replacing the 2-(4-aminophenyl)ethylamine of Example 11, step a, with the product of the previous step, the trifluoroacetate salt of the title compound was prepared. $^1$H NMR (300 MHz, DMSO-d$_6$): δ 10.4 (s, 2H), 9.8 (br s, 1H), 8.9 (br s, 1H), 8.7 (br s, 1H), 8.0 (d, 2H), 6.8-7.2 (m, 10H), 6.4 (d, 1H), 6.2 (br s, 1H), 5.2 (d, 1H), 2.8-3.1 (m, 6H), 2.3-2.7(m, 8H); m/z: [M+H$^+$] calcd for C$_{29}$H$_{34}$N$_4$O$_3$, 486.61; found 487.5.

Example 13

Synthesis of 5-[(R)-2-(2-{4-[4-(2-amino-2-methyl-propyl)-phenylamino]-phenyl}-ethylamino)-1-hydroxy-ethyl]-8-hydroxy-1H-quinolin-2-one a. Preparation of 1,1-dimethyl-2-(4-nitro-phenyl)-ethylamine α,α-Dimethylphenethylamine hydrochloride (20 g, 108 mmol) was dissolved in concentrated sulfuric acid (40 mL). The solution was cooled to −10° C. Nitric acid (31 mL, 90%) was added dropwise over a 30 min period while maintaining a reaction tempurature below −5° C. The solution was stirred an addition 45 min then poured over ice and allowed to warm to room temperature over night. The product was collected via filtration (13.7 g). Aqueous sodium hydroxide(1 N) was added to the filtrate and the title compound was isolated as a clear oil.

b. Preparation of 4-(2-amino-2-methyl-propyl)-phenylamine

Palladium (0.136 g, 10% wt. on activated carbon) was added to a solution of the product of step a (1.36 g, 7.0 mmol) in methanol (20 mL). The slurry was stirred vigorously under 1 atmosphere of hydrogen for 6 h. The reaction mixture was filtered and the filtrate concentrated under reduced pressure to afford the title intermediate (1.04 g crude) which was used without further purification.

c. Synthesis of 5-[(R)-2-(2-{4-[4-(2-amino-2-methyl-propyl)-phenylamino]-phenyl}-ethylamino)-1-hydroxy-ethyl]-8-hydroxy-1H-quinolin-2-one Using procedures similar to those described for Example 11, except replacing the 2-(4-aminophenyl)ethylamine of Example 11, step a, with the product of the previous step, the trifluoroacetate salt of the title compound was prepared. $^1$H NMR (300 MHz, DMSO-d$_6$): δ 10.4 (d, 2H), 8.8 (br s, 1H), 8.65 (br s, 1H), 8.0 (d, 2H), 7.7 (s, 3H), 6.8-7.0 (m, 8H), 6.4 (d, 1H), 6.1 (br s, 1H), 5.2 (d, 1H), 3 (m, 4H), 2.7(m, 2H), 2.6 (s, 2H), 1.0 (s, 6H); m/z: [M+H$^+$] calcd for C$_{29}$H$_{34}$N$_4$O$_3$, 486.61; found 487.5.

Example 14

Synthesis of N-{5-[(R)-2-(2-{4-[4-(2-amino-2-methyl-propoxy)-phenylamino]-phenyl}-ethylamino)-1-hydroxy-ethyl]-2-hydroxy-phenyl}-formamide a. Preparation of [4-(2-amino-2-methyl-propoxy-phenyl]-[4-(2-aminoethyl)-phenyl]-amine A mixture of 4-(2-amino-2-methyl-propoxy)-phenylamine (1.0 g, 5.5 mmol) (the freebase of the intermediate of Example 1, part a), 4-bromophenethylamine (1.1 g, 1 equiv), and sodium tert-butoxide (1.9 g, 3.5 equiv) in toluene (30 mL) was stirred at 90° C. until a homogenous solution was obtained. Tris(dibenzylideneacetone)dipalladium(0) (252 mg, 0.05 equiv) was added, followed by rac-2,2'-bis(diphenylphosphino)-1,1'-binapthyl (516 mg, 0.015 equiv). The reaction mixture was stirred at 90° C. for 16 h, then allowed to cool. The solution was diluted with ethyl acetate (100 mL), washed (1:1 saturated aqueous sodium chloride:water (100 mL), then extracted into 6 M hydrochloric acid (100 mL). The aqueous layer was washed with ethyl acetate (2×100 mL), then diluted with isopropyl acetate (100 mL). The mixture was cooled to 0° C. and neutralized with sodium hydroxide (13 g in 20 mL of water). The aqueous layer was removed and the organic layer washed (1:1 saturated aqueous sodium chloride:water, 100 mL), dried over sodium sulfate, and evaporated to afford the title intermediate (1.3 g crude).

b. Preparation of N-{5-[(R)-2-(2-{4-[4-(2-amino-2-methyl-propoxy)-phenylamino]-phenyl}-ethylamino)-1-(tert-butyl-dimethyl-silanyloxy)-ethyl]-2-benzyloxy-phenyl}-formamide A mixture of N-[5-((R)-2-bromo-1-(tert-butyl-dimethylsilanyloxy)-ethyl) -2-benzyloxy-phenyl]-formamide (2.0 g, 4.35 mmol), the product of the previous step (1.3 g, 1 equiv), potassium carbonate (2.4 g, 4 equiv) and sodium iodide (718 mg, 1.1 equiv) in dimethylsulfoxide (8 mL) was heated at 140° C. for 20 min. The mixture was allowed to cool, diluted with water (20 mL) and extracted with ethyl acetate (2×20 mL). The organics were washed with saturated aqueous sodium chloride (20 mL), dried over sodium sulfate, and evaporated. The residue was purified by reverse phase HPLC to afford the title intermediate (500 mg, 0.73 mmol, 17% yield).

c. Synthesis of N-{5-[(R)-2-(2-{4-[4-(2-amino -2-methyl-propoxy)-phenylamino]-phenyl}-ethylamino)-1-hydroxy-ethyl]-2-hydroxy-phenyl}-formamide Using procedures similar to those described for Example 1, steps c and d, the intermediate of step b was transformed to the title compound. m/z: [M+H$^+$] calcd for C$_{27}$H$_{35}$N$_4$O$_4$, 479.3; found 479.3.

Example 15

Synthesis of 5-[(R)-2-(2-{4-[3-(2-amino-ethyl)-4-methoxy-phenylamino]-phenyl}-ethylamino)-1-hydroxy-ethyl]-8-hydroxy-1H-quinolin-2-one a. Preparation of 5-{(R)-2[2-(4-amino-phenyl)-ethylamino]-1-(tert-butyl-dimethyl-silanyloxy)-ethyl]-8-benzyloxy-1H-quinolin-2-one A mixture of 5-(2-bromo-1-(tert-butyl-dimethyl-silanyloxy)-ethyl)-8-benzyloxy-1H-quinolin-2-one (5.0 g, 1.0 equiv) and 2-(4-aminophenyl)ethylamine (2.8 g, 2.0 equiv) in dimethylsulfoxide (10 mL) was heated at 100° C. for 12 h. The reaction mixture was cooled to 20° C., and the resulting red oil was diluted with ethyl acetate (200 mL) and extracted with two portions water (200 mL). The organic layer was washed with two portions of (1:1 10% aqueous acetic acid and saturated aqueous sodium chloride (200 mL). The organic layer was basified by carefully extracting with two portions of saturated sodium bicarbonate (200 mL), followed by saturated sodium chloride (200 mL). The resulting organic solution was treated with anhydrous sodium sulfate, and the solvent was removed under reduced pressure to afford the title intermediate (5.1 g) which was used without further purification.

b. Preparation of 5-[(R)-2-(2-{4-[3-(2-amino -ethyl)-4-methoxy-phenylamino]-phenyl}-ethylamino)-1-(tert-butyl-dimethyl-silanyloxy)-ethyl]-8-benzyloxy-1H-quinolin-2-one A mixture of the product of the previous step (0.500 g, 1.0 equiv), 5-bromo -2-methoxyphenethylamine hydrobromide (0.343 g, 1.2 equiv), and sodium tert-butoxide (0.397 g, 4.5 equiv) in toluene (10 mL) was stirred at 90° C. until a homogenous solution was obtained. Palladium tris(dibenzylideneacetone) (0.0042 g, 0.05 equiv) was added, followed by rac-2,2'-bis(diphenylphosphino)-1,1'-binapthyl (0.0086 g, 0.15 equiv). The reaction mixture was stirred at 90° C. for 5 h, then allowed to cool to 20° C. The solution was diluted with dichloromethane (100 mL) and washed with water (2×100 mL). The organic solution was dried over sodium sulfate. The reaction mixture was filtered and the solvent was removed under reduced pressure to give the title intermediate (1.0 g) as a dark brown solid, which was used without further purification.

c. Preparation of 5-[(R)-2-(2-{4-[3-amino-ethyl)-4-methoxy-phenylamino]-phenyl}-ethylamino)-1-hydroxy)-ethyl]-8-benzyloxy-1H-quinolin-2-one The crude solid (1.0 g) from the previous step was treated with triethylamine trihydrofluoride (0.70 mL) in tetrahydrofuran (10 mL) at room temperature for 5 h. The mixture was diluted with dichloromethane (100 mL) and extracted with 0.1 M NaOH (2×100 mL), followed by saturated aqueous sodium chloride (100 mL). The organic layer was treated with anhydrous sodium sulfate and the solvent was dried under reduced pressure. The resulting solid was purified by reverse phase HPLC and isolated as its trifluoroacetate salt by lyophilization to give the title intermediate (200 mg).

d. Synthesis of 5-[(R)-2-(2-{4-[3-(2-amino-ethyl) -4-methoxy-phenylamino]-phenyl}-ethylamino)-1-hydroxy)-ethyl]-8-hydroxy-1H-quinolin-2-one Palladium (10 mg, 10% w/w on carbon) followed by methanol (5 mL) was added to the intermediate of the previous step (50 mg) and the slurry was stirred vigorously under a hydrogen atmosphere for 5 h. The reaction mixture was filtered and the filtrate was concentrated under reduced pressure to afford the title compound (42.0 mg), which was purified by reverse phase HPLC and isolated as its trifluoroacetate salt by lyophilization. m/z: [M+H$^+$] calcd for $C_{28}H_{32}N_4O_4$, 489.3; found 489.5

Example 16

Synthesis of N-{5-[(R)-2-(2-{4-[3-(2-amino -ethyl)-4-methoxy-phenylamino]-phenyl}-ethylamino)-1-hydroxy-ethyl]-2-hydroxy-phenyl}-formamide Using procedures similar to those described for Example 15, except replacing the 5-(2-bromo-1-(tert-butyl-dimethyl-silanyloxy)-ethyl)-8-benzyloxy-1H-quinolin-2-one with N-[5-((R)-2-bromo-1-(tert-butyl-dimethyl-silanyloxy)-ethyl)-2-benzyloxy-phenyl]-formamide, the title compound was prepared. m/z: [M+H$^+$] calcd for $C_{26}H_{32}N_4O_4$, 465.3; found 465.3

Example 17

Figure 2:
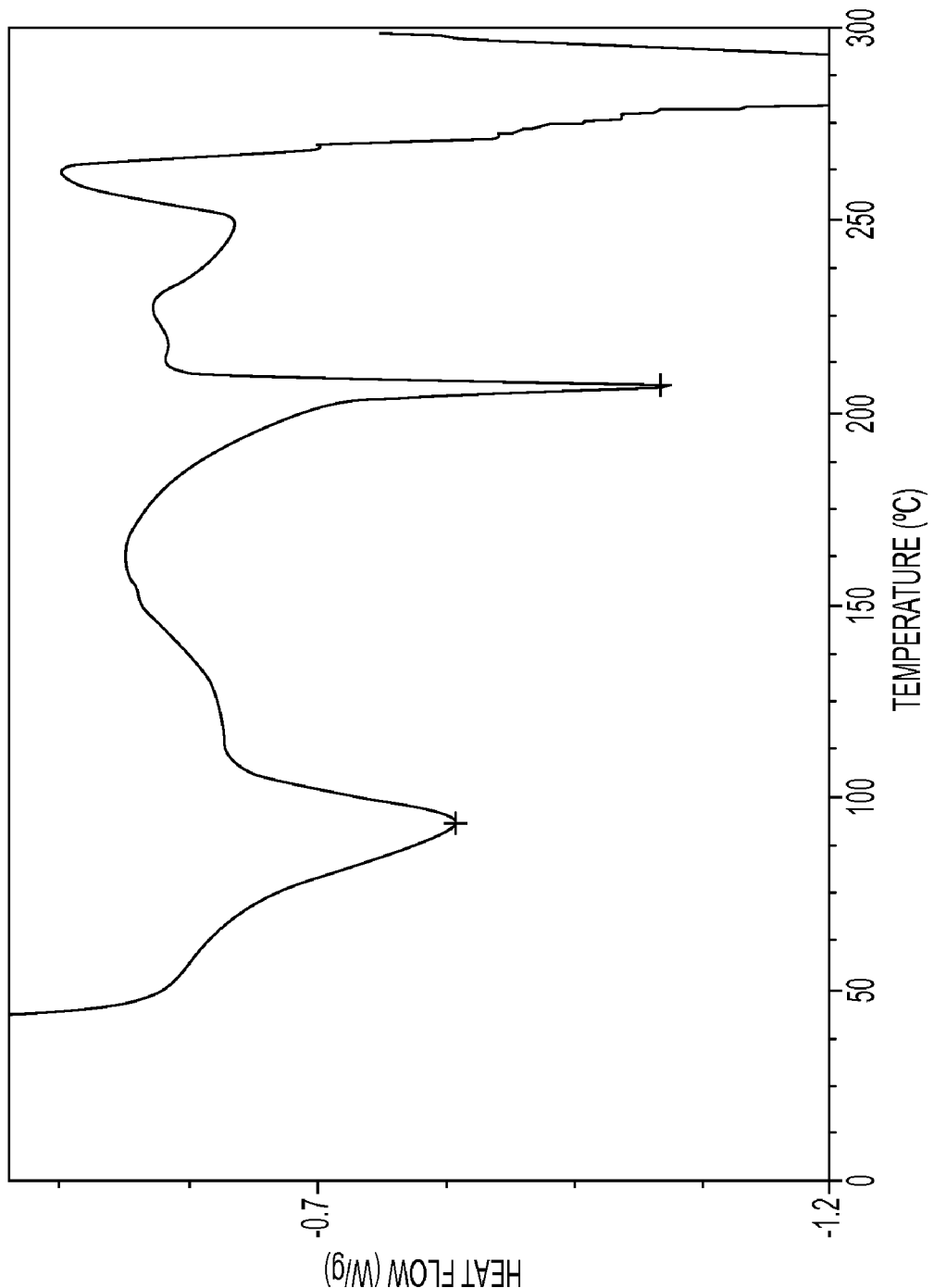
FIG. 2 is a differential scanning calorimetry trace of the product of Example 17b.
Figure 3:
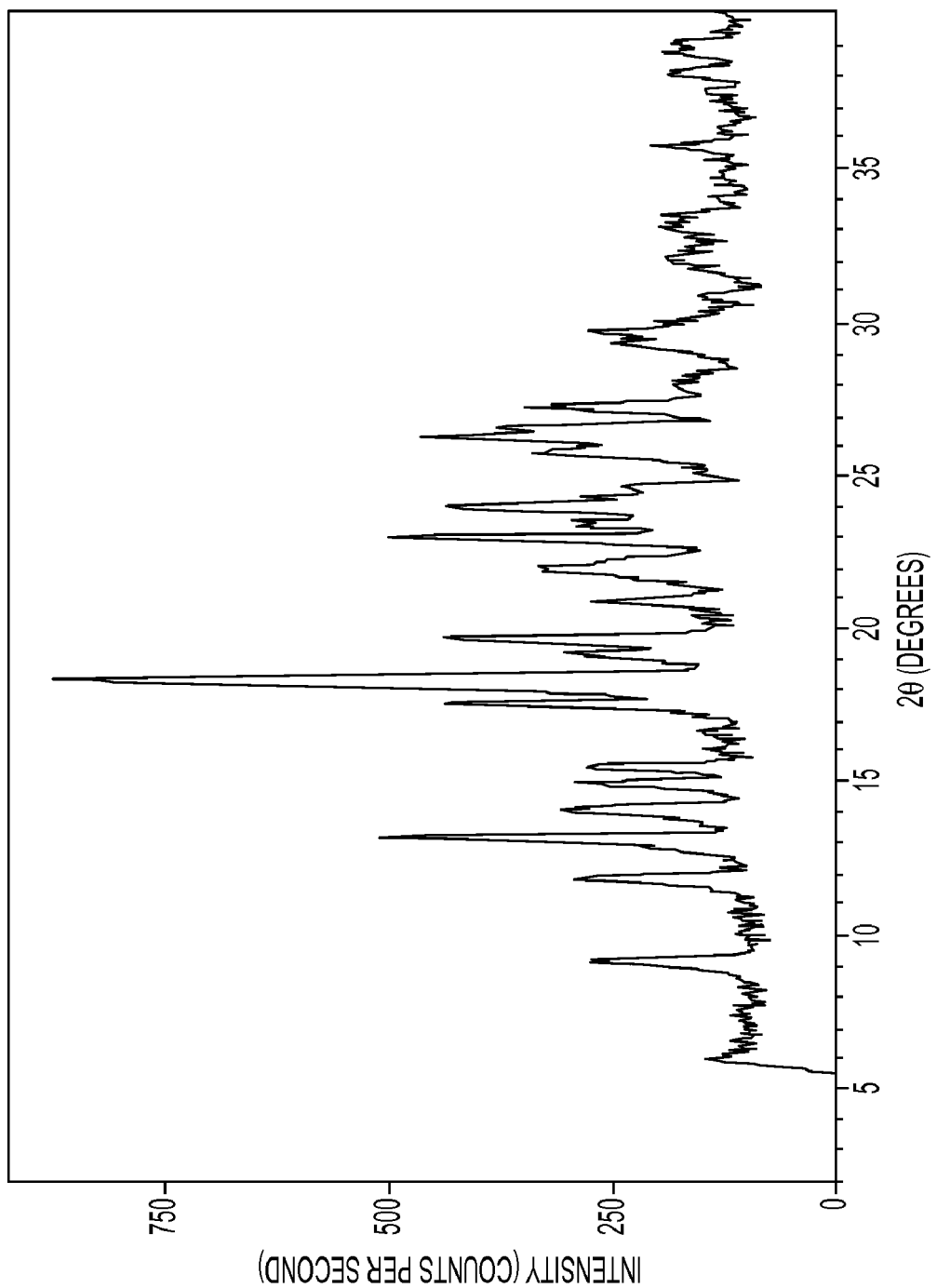
FIG. 3 is an x-ray powder diffraction pattern of the product of Example 17c.
Figure 4:
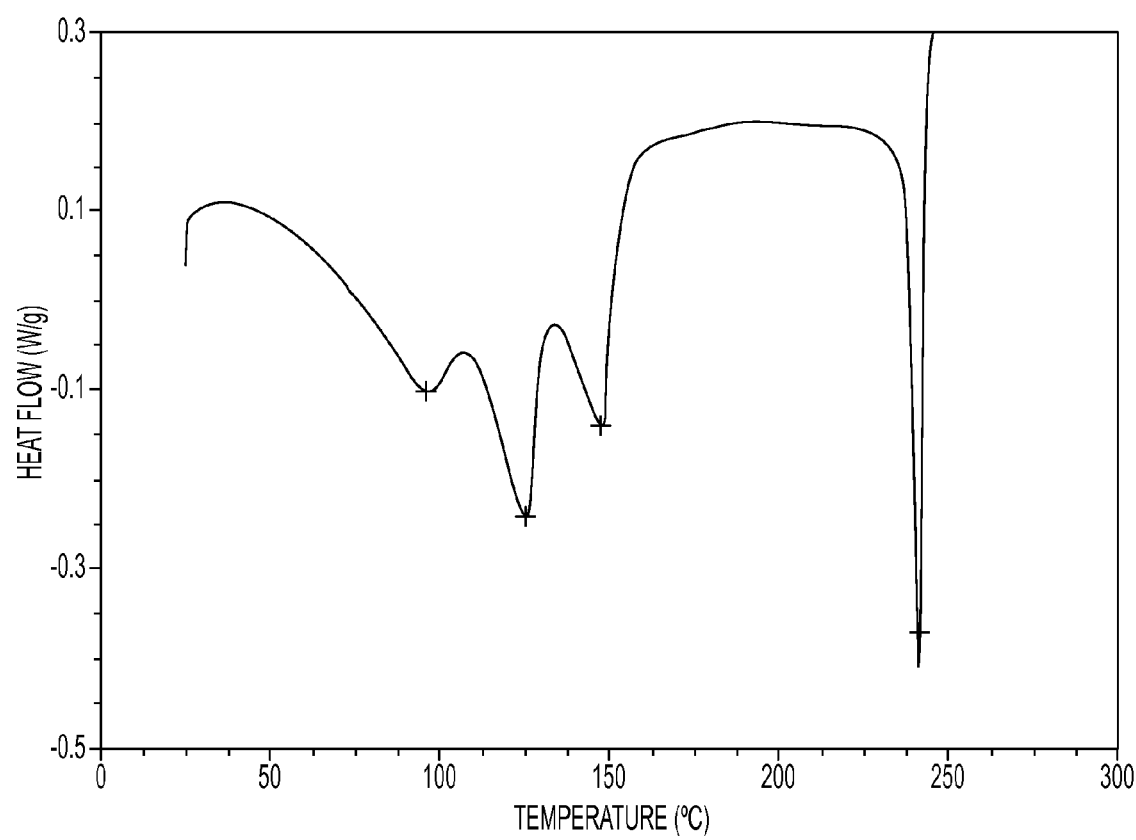
FIG. 4 is a differential scanning calorimetry trace of the product of Example 17c.
Figure 5:
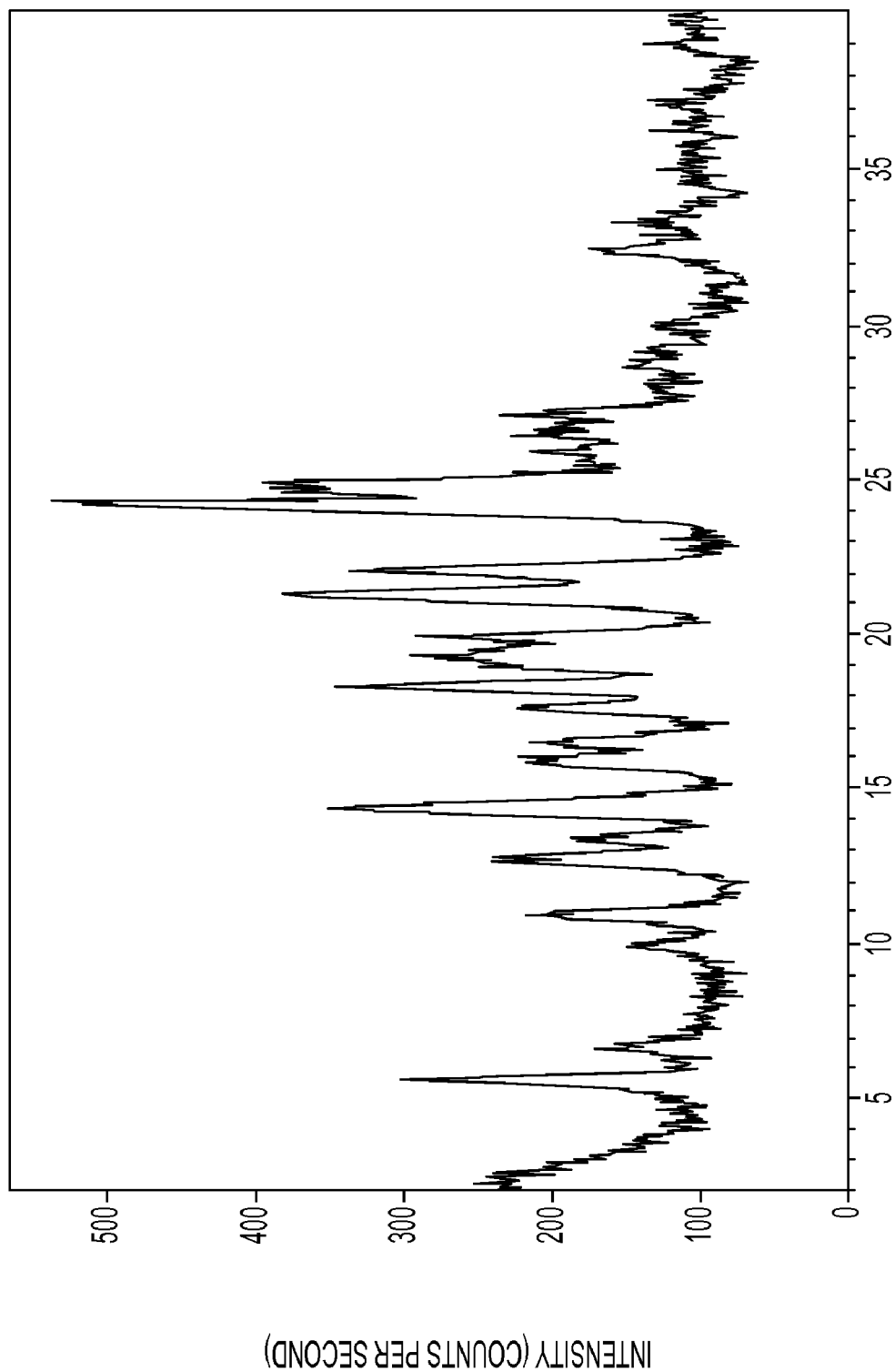
FIG. 5 is an x-ray powder diffraction pattern of the product of Example 17d.
Figure 6:
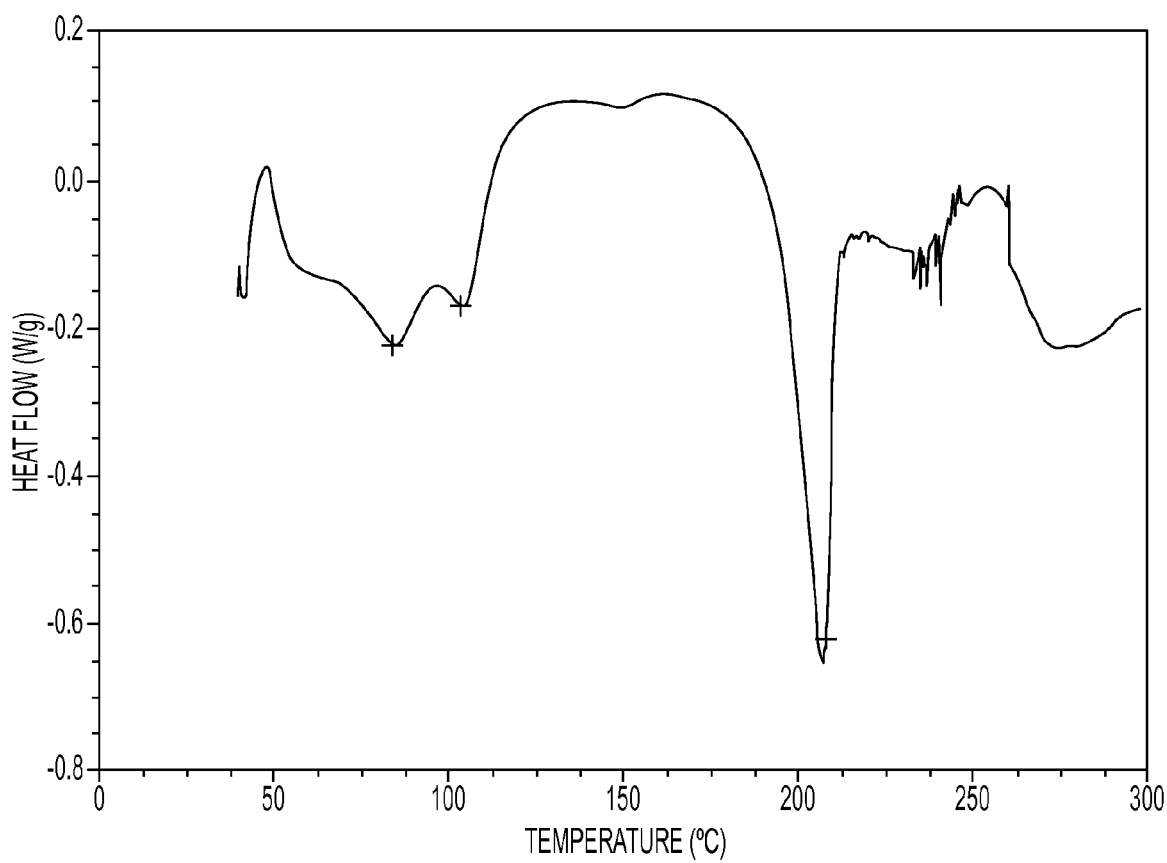
FIG. 6 is a differential scanning calorimetry trace of the product of Example 17d.

Salts of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one a. Preparation of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one free base Aqueous ammonium bicarbonate (10%) solution (50 mL) was added in one portion to a solution of the product of Example 1, 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one trifluoroacetate, (1.80 g, 2.1 mmol) in ethanol (6 mL). The solution was stirred at room temperature for 1 h. The resultant solid was filtered and dried under reduced pressure to afford the title compound (0.84 g, 1.67 mmol, 80%) as a yellow solid.

b. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one sulfate The free base produced as in the previous step (5.85 g, 11.6 mmol) was dissolved in acetonitrile:water (200 mL:60 mL) at 90° C. and filtered to remove remaining solid particles. The filtrate was re-heated to 90° C. and a solution of concentrated sulfuric acid (2 mL) in acetonitrile:water (18 mL:2 mL) was added. The solution was allowed to cool to room temperature over 2 h, then cooled in an ice/water bath to 10° C. The solid was filtered and dried under reduced pressure to afford the crude title salt (5.70 g, 82%). The material (5.70 g) was re-dissolved in acetonitrile:water (120 mL:410 mL) at 90°C., and again allowed to cool to room temperature over 2 h. The slurry was cooled in an ice/water bath to 10° C., the solid filtered and dried under reduced pressure to afford a hydrate of the title salt (4.40 g, 63% overall) as an off-white powder. The x-ray powder diffraction (XRPD) pattern of the product is shown in FIG. 1. The differential scanning calorimetry trace of the product is shown in FIG. 2.

c. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one napadisylate To a solution of the free base produced as in part a (23 mg, 0.046 mmol) in isopropanol:water (1.8 mL:0.2 mL) at 60° C., was added 1,5-napthalene-disulfonic acid tetrahydrate (33 mg, 2 equiv), affording a white precipitate. The temperature was raised to 70° C. and another 1 mL of water was added to afford a clear solution. After cooling to room temperature, the slurry was filtered and dried to afford the title salt (25 mg, 63%) as a white powder. The XRPD pattern of the product is shown in FIG. 3. The differential scanning calorimetry trace of the product is shown in FIG. 4.

d. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one oxalate To a solution of the free base produced as in part a (100 mg, 0.2 mmol) in isopropanol:water (3.6 mL:0.4 mL) at 60° C. was added oxalic acid (50 mg, 2 equiv), affording a white precipitate. The temperature was raised to 70° C. and another 4 mL of water was added to afford a clear solution. After cooling to room temperature, the slurry was filtered and dried to afford the title salt (82 mg, 65%) as an off-white powder. The XRPD pattern of the product is shown in FIG. 5. The differential scanning calorimetry trace of the product is shown in FIG. 6.

e. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methyl-cinnamate 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (0.21 g) was dissolved in a mixture of tetrahydrofuran (1.2 mL) and water (1.2 mL). 4-methyl-cinnamic acid (0.07 g, predominantly trans) was added to the stirred solution at room temperature and it dissolved. After approximately 10 min, crystallization occurred. The slurry was stirred overnight and filtered. The cake was washed with aqueous tetrahydrofuran (1:1 THF:water, 2×0.4 mL, 1×0.2 mL) to afford the title compound which was dried overnight under vacuum at 45° C. (yield: 0.207 g). $^1$H NMR (400 MHz, DMSO-$d_6$; DMSO-$d_5$ as reference at δ (ppm) 2.5). δ (ppm): 1.22 (6H) s; 2.30 (3H) s; 2.64 (2H) t J=6.6 Hz; 2.72-2.86 (4H) m; 3.74 (2H) s; 5.09 (1H) m; 6.43 (1H) d J=15.9 Hz; 6.49 (1H) d J=10.0 Hz; 6.86 (4H) m; 6.93-7.03 (5H) m; 7.06 (1H) d J=7.8 Hz; 7.17 (2H) d J=7.8 Hz; 7.34 (1H) d J=15.9 Hz; 7.45 (2H) d J=7.8 Hz; 7.75 (1H) s; 8.19 (1H) d J=10.0 Hz. The crystalline product was characterized by XRPD and DSC.

f. Synthesis of 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one 4-methyl-cinnamate 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one (17.77 g) was dissolved in a mixture of tetrahydrofuran (89 mL) and water (89 mL). 4-methyl-cinnamic acid (6.02 g, predominantly trans) was weighed out and about one-quarter was added to the free base solution followed by seed crystals, obtained by the procedure of part e. The mixture was stirred and the remaining acid was added in portions over the following 1.5 h. The slurry was stirred for a further 4 h and then the slurry was filtered. The cake was washed with aqueous tetrahydrofuran (1:1 THF:water, 36 mL) and then with tetrahydrofuran (2×18 mL) to afford the title compound which was dried overnight under vacuum at 40-50° C. (yield: 16.916 g). $^1$H NMR (400 MHz, CD$_3$OD; TMS as reference at δ (ppm) 0) δ (ppm): 1.39 (6H) s; 2.32 (3H) s; 2.79 (2H) t J=7.2 Hz; 2.92-3.03 (4H) m; 3.87 (2H) s; 5.25 (1H) d of d J=3.9 and 8.8 Hz; 6.44 (1H) d J=15.9 Hz; 6.63 (1H) d J=9.8 Hz; 6.86-6.93 (4H) m; 6.96 (1H) d J=8.3 Hz; 6.99-7.05 (4H) m; 7.15 (2H) d J=7.8 Hz; 7.19 (1H) d J=8.3 Hz; 7.36 (1H) d J=15.9 Hz; 7.38 (2H) d J=7.6 Hz; 8.34 (1H) d J=9.8 Hz. The crystalline product was characterized by XRPD and DSC.

g. Analytical Methods

X-ray powder diffraction patterns of FIGS. 1, 3, and 5 were obtained with a Rigaku diffractometer using Cu Kα (30.0 kV, 15.0 mA) radiation. The analysis was performed with the goniometer running in continuous-scan mode of 3° per min with a step size of 0.03° over a range of 2 to 45°. Samples were prepared on quartz specimen holders as a thin layer of powdered material. The instrument was calibrated with a silicon metal standard.

Differential scanning calorimetry traces of FIGS. 2, 4, and 6 were obtained with a TA instruments model DSCQ10. Samples were placed in sealed aluminum pans for analysis with an empty pan serving as the reference. Samples were equilibrated at 30° C. and heated at 5° C. per minute to a temperature of 300° C. The instrument was calibrated with an indium standard.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:
1. A method of treating asthma or chronic obstructive pulmonary disease in a mammal, the method comprising administering to the mammal a pharmaceutical composition comprising a pharmaceutically-acceptable carrier and a compound of formula (II):

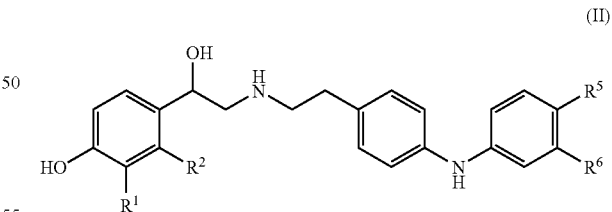

(II)

wherein:
$R^1$ and $R^2$ taken together are —NHC(=O)CH=CH— or —CH=CHC(=O)NH—;
one of $R^5$ and $R^6$ is —[O—C$_{1-6}$alkylenyl]$_n$-NR$^{10}$R$^{11}$ or C$_{1-6}$alkylenyl-NR$^{12}$R$^{13}$,
and the other of $R^5$ and $R^6$ is selected from hydrogen, hydroxy, C$_{1-4}$alkoxy, and C$_{1-4}$alkyl, wherein C$_{1-4}$alkyl is optionally substituted with halo,
wherein
each of $R^{10}$, $R^{11}$, $R^{12}$, and $R^{13}$ is independently hydrogen or C$_{1-4}$alkyl; or $R^{10}$ and $R^{11}$, together with the nitrogen atom to which they are attached, or $R^{10}$, together with the nitrogen atom to which it is attached and a carbon atom of the adjacent $C_{1-6}$alkylenyl, or $R^{12}$ and $R^{13}$, together with the nitrogen atom to which they are attached, or $R^{12}$, together with the nitrogen atom to which it is attached and a carbon atom of the adjacent $C_{1-6}$alkylenyl, form a heterocyclic or heteroaryl ring having from 5 to 7 ring atoms and optionally containing an additional heteroatom selected from oxygen, nitrogen, and sulfur, wherein nitrogen is optionally substituted with —S(O)$_2$—C$_{1-4}$alkyl; and n is 1 or 2;

or a pharmaceutically-acceptable salt or stereoisomer thereof.

2. The method of claim 1 wherein:
$R^5$ is selected from —O—C$_{1-6}$alkylenyl-NR$^{10}$R$^{11}$ and C$_{1-6}$alkylenyl-NR$^{12}$R$^{13}$ and R$^6$ is hydrogen; or
$R^5$ is C$_{1-4}$alkoxy and R$^6$ is —C$_{1-6}$alkylenyl-NR$^{12}$R$^{13}$,
wherein each of $R^{10}$, $R^{11}$, $R^{12}$ and $R^{13}$ is independently hydrogen or C$_{1-4}$alkyl, or $R^{10}$ and $R^{11}$, together with the nitrogen atom to which they are attached, form a piperazinyl ring.

3. The method of claim 2 wherein R$^5$ is —O—C$_{1-6}$alkylenyl-NR$^{10}$R$^{11}$ and R$^6$ is hydrogen.

4. The method of claim 1 wherein the stereochemistry at the alkylene carbon bearing the hydroxyl group is (R).

5. The method of claim 1 wherein the compound of formula (II) is selected from:
5-[(R)-2-(2-{4-[4-(2-amino-2-methyl -propoxy)-phenylamino]-phenyl}-ethylamino)-1-hydroxy-ethyl]-8-hydroxy-1H-quinolin-2-one;
8-hydroxy-5-[(R)-1-hydroxy-2-(2-{4-[4-(2-piperazin-1-yl-ethoxy)-phenylamino]-phenyl}-ethylamino)-ethyl]-1H-quinolin-2-one;
5-[(R)-2-(2-{4-[4-(2-amino-ethyl)-phenylamino]-phenyl}-ethylamino)-1-hydroxy-ethyl]-8-hydroxy-1H-quinolin-2-one;
5-[(R)-2-(2-{4-[4-(2-dimethylamino-ethyl) -phenylamino]-phenyl}-ethylamino)-1-hydroxy-ethyl]-8-hydroxy-1H-quinolin-2-one; and
5-[(R)-2-(2-{4-[3-(2amino-ethyl)-4-methoxy -phenylamino]-phenyl}-ethylamino)-1-hydroxy-ethyl]-8-hydroxy-1H-quinolin-2-one; and
pharmaceutically-acceptable salts thereof.

6. The method of claim 1 wherein the compound of formula (II) is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one, or a pharmaceutically-acceptable salt thereof.

7. The method of claim 6 wherein the compound of formula (II) is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one sulfate.

8. The method of claim 6 wherein the compound of formula (II) is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one napadisylate.

9. The method of claim 6 wherein the compound of formula (II) is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one oxalate.

10. The method of claim 1 wherein the method comprising administering the compound of formula (II) by inhalation.

11. The method of claim 1 further comprising administering one or more other therapeutic agents wherein the other therapeutic agent is a corticosteroid or an anticholinergic agent.

12. A method of providing bronchoprotection in a mammal, the method comprising administering to the mammal a pharmaceutical composition comprising a pharmaceutically-acceptable carrier and a compound of formula (II):

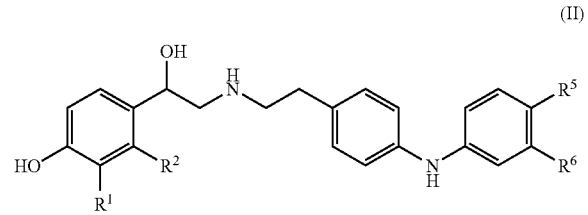

(II)

wherein:
$R^1$ and $R^2$ taken together are —NHC(=O)CH=CH— or —CH=CHC(=O)NH—;
one of $R^5$ and $R^6$ is —[O—C$_{1-6}$alkylenyl]$_n$-NR$^{10}$R$^{11}$ or C$_{1-6}$alkylenyl-NR$^{12}$R$^{13}$,
and the other of $R^5$ and $R^6$ is selected from hydrogen, hydroxy, C$_{1-4}$alkoxy, and C$_{1-4}$alkyl,
wherein C$_{1-4}$alkyl is optionally substituted with halo,
wherein
each of $R^{10}$, $R^{11}$, $R^{12}$, and $R^{13}$ is independently hydrogen or C$_{1-4}$alkyl; or
$R^{10}$ and $R^{11}$, together with the nitrogen atom to which they are attached, or $R^{10}$, together with the nitrogen atom to which it is attached and a carbon atom of the adjacent C$_{1-6}$alkylenyl, or $R^{12}$ and $R^{13}$, together with the nitrogen atom to which they are attached, or $R^{12}$, together with the nitrogen atom to which it is attached and a carbon atom of the adjacent C$_{1-6}$alkylenyl, form a heterocyclic or heteroaryl ring having from 5 to 7 ring atoms and optionally containing an additional heteroatom selected from oxygen, nitrogen, and sulfur, wherein nitrogen is optionally substituted with —S(O)$_2$—C$_{1-4}$alkyl; and n is 1 or 2;

or a pharmaceutically-acceptable salt or stereoisomer thereof.

13. The method of claim 12 wherein:
$R^5$ is selected from —O—C$_{1-6}$alkylenyl-NR$^{10}$R$^{11}$ and C$_{1-6}$alkylenyl-NR$^{12}$R$^{13}$ and R$^6$ is hydrogen; or
$R^5$ is C$_{1-4}$alkoxy and R$^6$ is —C$_{1-6}$alkylenyl-NR$^{12}$R$^{13}$,
wherein each of $R^{10}$, $R^{11}$, $R^{12}$ and $R^{13}$ is independently hydrogen or C$_{1-4}$alkyl, or $R^{10}$ and $R^{11}$, together with the nitrogen atom to which they are attached, form a piperazinyl ring.

14. The method of claim 13 wherein R$^5$ is —O—C$_{1-6}$alkylenyl-NR$^{10}$R$^{11}$ and R$^6$ is hydrogen.

15. The method of claim 12 wherein the compound of formula (II) is selected from:
5-[(R)-2-(2-{4-[4-(2-amino-2-methyl -propoxy)-phenylamino]-phenyl}-ethylamino)-1-hydroxy-ethyl]-8-hydroxy-1H-quinolin-2-one;
8-hydroxy-5-[(R)-1-hydroxy-2-(2-{4-[4-(2-piperazin-1-yl-ethoxy)-phenylamino]-phenyl}-ethylamino)-ethyl]-1H-quinolin-2-one;
5-[(R)-2-(2-{4-[4-(2-amino-ethyl)-phenylamino]-phenyl}-ethylamino)-1-hydroxy-ethyl]-8-hydroxy-1H-quinolin-2-one;

5-[(R)-2-(2-{4-[4-(2-dimethylamino-ethyl)-phenylamino]-phenyl}-ethylamino)-1-hydroxy-ethyl]-8-hydroxy-1H-quinolin-2-one; and 5-[(R)-2-(2-{4-[3-(2-amino-ethyl)-4-methoxy-phenylamino]-phenyl}-ethylamino)-1-hydroxy-ethyl]-8-hydroxy-1H-quinolin-2-one; and pharmaceutically-acceptable salts thereof.

16. The method of claim 12 wherein the compound of formula (II) is 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one, or a pharmaceutically-acceptable salt thereof.

17. The method of claim 12 wherein the method comprising administering the compound of formula (II) by inhalation.

18. The method of claim 12 further comprising administering one or more other therapeutic agents wherein the other therapeutic agent is a corticosteroid or an anticholinergic agent.

19. A method of agonizing a β$_2$ adrenergic receptor in a mammal, the method comprising administering to the mammal a pharmaceutical composition comprising a pharmaceutically-acceptable carrier and a compound of formula (II):

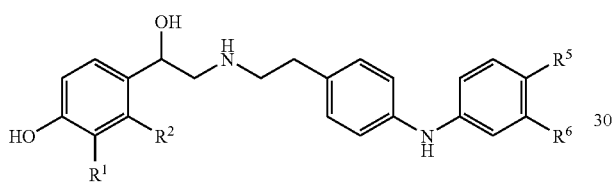

(II)

wherein:
$R^1$ and $R^2$ taken together are —NHC(=O)CH=CH— or —CH=CHC(=O)NH—;
one of $R^5$ and $R^6$ is —[O—C$_{1-6}$alkylenyl]$_n$-NR$^{10}$R$^{11}$ or C$_{1-6}$alkylenyl-NR$^{12}$R$^{13}$,
and the other of $R^5$ and $R^6$ is selected from hydrogen, hydroxy, C$_{1-4}$alkoxy, and C$_{1-4}$alkyl, wherein C$_{1-4}$alkyl is optionally substituted with halo,
wherein
each of $R^{10}$, $R^{11}$, $R^{12}$, and $R^{13}$ is independently hydrogen or C$_{1-4}$alkyl; or
$R^{10}$ and $R^{11}$, together with the nitrogen atom to which they are attached, or $R^{10}$, together with the nitrogen atom to which it is attached and a carbon atom of the adjacent C$_{1-6}$alkylenyl, or $R^{12}$ and $R^{13}$, together with the nitrogen atom to which they are attached, or $R^{12}$, together with the nitrogen atom to which it is attached and a carbon atom of the adjacent C$_{1-6}$alkylenyl, form a heterocyclic or heteroaryl ring having from 5 to 7 ring atoms and optionally containing an additional heteroatom selected from oxygen, nitrogen, and sulfur, wherein nitrogen is optionally substituted with —S(O)$_2$—C$_{1-4}$alkyl; and
n is 1 or 2;
or a pharmaceutically-acceptable salt or stereoisomer thereof.

20. The method of claim 19 wherein the compound of formula (II) is selected from:

5-[(R)-2-(2-{4-[4-(2-amino-2-methyl-propoxy)-phenylamino]-phenyl}-ethylamino)-1-hydroxy-ethyl]-8-hydroxy-1H-quinolin-2-one;

8-hydroxy-5-[(R)-1-hydroxy-2-(2-{4-[4-(2-piperazin-1-yl-ethoxy)-phenylamino]-phenyl}-ethylamino)-ethyl]-1H-quinolin-2-one;

5-[(R)-2-(2-{4-[4-(2-amino-ethyl)-phenylamino]-phenyl}-ethylamino)-1-hydroxy-ethyl]-8-hydroxy-1H-quinolin-2-one;

5-[(R)-2-(2-{4-[4-(2-dimethylamino-ethyl)-phenylamino]-phenyl}-ethylamino)-1-hydroxy-ethyl]-8-hydroxy-1H-quinolin-2-one; and 5-[(R)-2-(2-{4-[3-(2-amino-ethyl)-4-methoxy-phenylamino]-phenyl}-ethylamino)-1-hydroxy-ethyl]-8-hydroxy-1H-quinolin-2-one; and pharmaceutically-acceptable salts thereof.

* * * * *